(12) United States Patent
Simonet

(10) Patent No.: US 6,268,212 B1
(45) Date of Patent: Jul. 31, 2001

(54) TISSUE SPECIFIC TRANSGENE EXPRESSION

(75) Inventor: William Scott Simonet, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 08/221,767

(22) Filed: Mar. 31, 1994

Related U.S. Application Data

(63) Continuation-in-part of application No. 08/141,322, filed on Oct. 18, 1993, now abandoned.

(51) Int. Cl.[7] .......................... C07H 21/00; C12N 15/63; C12N 15/74; C12N 15/85
(52) U.S. Cl. ...................... 435/320.1; 435/325; 435/455; 435/471; 536/23.1; 536/23.5; 536/24.1
(58) Field of Search ................................. 536/23.1, 23.5, 536/24.1; 800/2, DIG. 1; 435/240.1, 240.3, 320.1, 172.3, 325, 455, 471; 935/6, 8, 22, 34, 66

(56) References Cited

FOREIGN PATENT DOCUMENTS

| 589851 | 3/1994 | (EP) . |
|---|---|---|
| WO88/10304 | 12/1988 | (WO) . |
| WO 90/08771 | 9/1990 | (WO) . |
| WO90/13655 | 11/1990 | (WO) . |

OTHER PUBLICATIONS

J D Smith et al. (1988) J Biol Chem 263:8300–8308.*
H S Lichenstein et al (1994) J Biol Chem 269:18149–18154.*
P Schmid et al (1991) Development 113:857–865.*
G Audesirk et al (1986) Biology :Life on Earth pp 353–367.*
JW Gordon et al (1981) Science 214:1244–1246.*
BKC Chow et al (1991) J Biol Chem. 266(28): 18927–18933.*
K Matsushima et al (1988) J Exp Med 167:1883–1893.*
N Mukaida et al (1989) J. Immunology 143:1366–1371.*
Fan et al., Overexpression of hepatic lipase in transgenic rabbits leads to a marked reduction of plasma high density lipoproteins and intermediate density lipoproteins, *Proc. Natl. Acad. Sci. USA*, vol. 91, pp. 8724–8728, Aug./1994.
Simonet et al., Long–term Impaired Neutrophil Migration in Mice Overexpressing Human Interleukin–8, *J. Clin. Invest.*, vol. 94, pp. 1310–1319, Sep./1994.
Dang et al., Structure of the Hepatic Control Region of the Human Apolipoprotein E/C–I Gene Locus, *J. of Biological Chemistry*, vol. 270, No. 38, Issue of Sep. 22, pp. 22577–22585, 1995.
Jan L. Breslow, Proc. Natl. Acad. Sci. USA, 90: p8314–8318, 1993, Transgenic Mouse Models of Lipoprotein Metabolism and Atherosclerosis.

Brooks et al., Circulation 86 (4 Suppl) 1992, Regulatory Elements of the Human Apolipoprotein B Gene Required for Tissue–Specific Expression in Transgenic Mice.
Burrows et al., Ann. N.Y. Acad. Sci., 629: p422–424, 1991, Intraperitoneal Injection of Human Recombinant Neutrophil–Activating Factor, Interleukin 8 . . .
Colditz et al., Journal of Leukocyte Biology, 48: p29–137, 1990, Neutrophil Accumulation and Plasma Leakage Induced In Vivo by Neutrophil–Activating Peptide–1.
Fazio et al., Circulation, 86: No. 4, 1992, Hepatic Expression of a Receptor–Binding–Defective Human Apolipoprotein E Variant Creates a Model of Type III Hyperlipoproteinemia in Transgenic Mice.
Fazio et al., Circulation, 84: No. 4, 1991, Expression of Human Apolipoprotein E Variants in Transgenic Mice.
Finch et al., Science, 245: p752–755, 1989, Human KGF Is FGF–Related with Properties of a Paracrine Effector of Epithelial Cell Growth.
Furutani et al., Biochemical and Biophysical Research Communications, 159: No. 1, 1989, Cloning and Sequencing of the cDNA For Human Monocyte Chemotactic and Activating Factor (MCAF).
Guo et al., The EMBO Journal, 12: No. 3 p973–986, 1993, Targeting Expression of Keratinocyte Growth Factor to Keratinocytes Elicits Striiing Change In Epithelial Differentiation In Transgenic Mice.
Graves et al., American Journal of Pathology, 140: No. 1, p9–14, 1992, Expression of Monocyte Chemotactic Protein–1 in Human Melanoma In Vivo.
Hammer et al., Science, 235: p53–58, 1987, Diversity of Alpha–Fetoprotein Gene Expression in Mice Is Generated by a Combination of Separate Enhancer Elements.
Leonard et al., The Journal of Investigative Dermatology, 96: No. 5, p690–694, 1991, Neutrophil Recruitment by Intradermally Injected Neutrophil Attractant/Activation Protein–1.
Leonard and Yoshimura, Immunology Today, 11: No. 3, p97–101, 1990, Human Monocyte Chemoattractant Protein–1 (MCP–1).
Marchese et al., Journal of Cellular Physiology, 144: p326–332, 1990, Human Keratinocyte Growth Factor Activity on Proliferation and Differentiation of Human Keratinocytes: Differentiation Response Distinguishes KGF from EGF Family.
Rubin et al., Proc. Natl. Acad. Sci. USA, 86: p802–806, 1989, Purification and Characterization of a Newly Identified Growth Factor Specific for Epithelial Cells.

(List continued on next page.)

Primary Examiner—Scott D. Priebe
Assistant Examiner—Ram R. Shukla
(74) Attorney, Agent, or Firm—Nancy A. Oleski; Steven M. Odre

(57) ABSTRACT

This invention provides a mammal with enhanced liver expression of a transgene. Also provided are 1) a nucleic acid sequence useful in enhancing liver specific expression of a transgene, and 2) a vector containing this nucleic acid sequence.

14 Claims, 8 Drawing Sheets

OTHER PUBLICATIONS

Shachter et al., Journal of Lipid Research, 34: 1699–1707, 1993, Localization of a liver–specific enhancer in the apolipoprotein E/C–1/C–11 gene locus.

Simonet et al., Journal of Biological Chemistry, 268: No. 11, Issue of Apr. 15, p8221–8229, 1993, A Far–downstream Hepatocyte–specific Control Region Directs Expression of the Linked Human Apolipoprotein E and C–I Genes in Transgenic Mice.

Simonet et al., Circulation, 84: No. 4, pII–18, 1991, Liver–Specific Regulation of the Human Apolipoprotein E/C–I Gene Locus in Transgenic Mice.

Simonet et al., Journal of Biological Chemistry, 266: No. 14, Issue of May 15, p8651–8654, 1991, Multiple Tissue–Specific Elements Control the Apolipoprotein E/C–I Gene Locus in Transgenic Mice.

Simonet et al., Journal of Biological Chemistry, 265: No. 19, Issue of Jul. 5, p10809–10812, 1990, In the Absence of a Downstream Element, the Apolipoprotein E Gene Is Expressed at High Levels in Kidneys of Transgenic Mice.

Taylor et al., Current Opinion in Lipidology, 2: p73–80, 1991, Expression of the Human Apolipoprotein E/Apolipoprotein C–I Gene Locus in Transgenic Mice.

Van Zee et al., Journal of Immunology, 148: No. 6, p1746–1752, 1992, Effects of Intravenous IL–8 Administration in Nonhuman Primates.

Vogels et al., Antimicrobial Agents and Chemotherapy, 37: No. 2, p276–280, 1993, Effects of Interleukin–8 on Nonspecific Resistance to Infection in Neutropenic and Normal Mice.

Walsh et al., Biotechnology, 16: p227–235, 1991, Apolipoprotein A–I Gene Expression in Transgenic Mice.

Zwahlen et al., International Review of Experimental Pathology, 34B: p27–42, 1993, In Vitro and In Vivo Activity and Pathophysiology of Human Interleukin–8 and Related Peptides.

* cited by examiner

FIG. 1

```
CTGCAGGCTC AGAGGCACAC AGGAGTTTCT GGGCTCACCC TGCCCCCTTC
CAACCCCTCA GTTCCCATCC TCCAGCAGCT GTTTGTGTGC TGCCTCTGAA
GTCCACACTG AACAAACTTC AGCCTACTCA TGTCCCTAAA ATGGGCAAAC
ATTGCAAGCA GCAAACAGCA AACACACAGC CCTCCCTGCC TGCTGACCTT
GGAGCTGGGG CAGAGGTCAG AGACCTCTCT GGGCCCATGC CACCTCCAAC
ATCCACTCGA CCCCTTGGAA TTTCGGTGGA GAGGAGCAGA GGTTGTCCTG
GCGTGGTTTA GGTAGTGTGA GAGGGTCCGG GTTCAAAACC ACTTGCTGGG
TGGGGAGTCG TCAGTAAGTG GCTATGCCCC GACCCCGAAG CCTGTTTCCC
CATCTGTACA ATGGAAATGA TAAAGACGCC CATCTGATAG GGTTTTTGTG
GCAAATAAAC ATTTGGTTTT TTTGTTTTGT TTTGTTTTGT TTTTGAGAT
GGAGGTTTGC TCTGTCGCCC AGGCTGGAGT GCAGTGACAC AATCTCATCT
CACCACAACC TTCCCCTGCC TCAGCCTCCC AAGTAGCTGG GATTACAAGC
ATGTGCCACC ACACCTGGCT AATTTTCTAT TTTTAGTAGA GACGGGTTTC
TCCATGTTGG TCAGCCTCAG CCTCCCAAGT AACTGGGATT ACAGGCCTGT
GCCACCACAC CCGGCTAATT TTTTCTATTT TTGACAGGGA CGGGGTTTCA
CCATGTTGGT CAGGCTGGTC TAGA
```

FIG. 4A

CCCCGAGTCT CTGCGCCTTC ACATAGTTGT CACAGGACTA AAGCAAATTG ATCCAGGGGG

AAACACTGTA GACCGTGTAT ATAAAAACAC TCTATAAACT GCAATGCTCA ATTCTTAGTA

TAACTATTGT TGTTGTATTG ATATTTATTA GTATTGGTGC TCACAAAAAG AGTCTAAATT

CCATAAGTCT TTATATTCAG GCTACTCTTT ATTTTGAAA ACTCATTTTC TATCACCTTT

TTCTATTTTA CTCCATATTG AGGCCTCATA AATCCAATTT TTTATTTCTT TCTTTTGTAA

```
ATGTGGTTTC TACAAAG ATG AAA CTA CTA AAA CTT ACA GGT TTT ATT TTT
                    Met Lys Leu Leu Lys Leu Thr Gly Phe Ile Phe
                    -21 -20                 -15

TTC TTG TTT TTT TTG ACT GAA TCC CTA ACC CTG CCC ACA CAA CCT CGG
Phe Leu Phe Phe Leu Thr Glu Ser Leu Thr Leu Pro Thr Gln Pro Arg
-10              -5                   1               5

GAT ATA GAG AAC TTC AAT AGT ACT CAA AAA TTT ATA GAA GAT AAT ATT
Asp Ile Glu Asn Phe Asn Ser Thr Gln Lys Phe Ile Glu Asp Asn Ile
                10              15                  20

GAA TAC ATC ACC ATC ATT GCA TTT GCT CAG TAT GTT CAG GAA GCA ACC
Glu Tyr Ile Thr Ile Ile Ala Phe Ala Gln Tyr Val Gln Glu Ala Thr
            25              30              35

TTT GAA GAA ATG GAA AAG CTG GTG AAA GAC ATG GTA GAA TAC AAA GAC
Phe Glu Glu Met Glu Lys Leu Val Lys Asp Met Val Glu Tyr Lys Asp
    40              45              50

AGA TGT ATG GCT GAC AAG ACG CTC CCA GAG TGT TCA AAA TTA CCT AAT
Arg Cys Met Ala Asp Lys Thr Leu Pro Glu Cys Ser Lys Leu Pro Asn
55              60              65              70

AAT GTT TTA CAG GAA AAA ATA TGT GCT ATG GAG GGG CTG CCA CAA AAG
Asn Val Leu Gln Glu Lys Ile Cys Ala Met Glu Gly Leu Pro Gln Lys
                75              80              85

CAT AAT TTC TCA CAC TGC TGC AGT AAG GTT GAT GCT CAA AGA AGA CTC
His Asn Phe Ser His Cys Cys Ser Lys Val Asp Ala Gln Arg Arg Leu
            90              95              100

TGT TTC TTC TAT AAC AAG AAA TCT GAT GTG GGA TTT CTG CCT CCT TTC
Cys Phe Phe Tyr Asn Lys Lys Ser Asp Val Gly Phe Leu Pro Pro Phe
            105             110             115

CCT ACC CTG GAT CCC GAA GAG AAA TGC CAG GCT TAT GAA AGT AAC AGA
Pro Thr Leu Asp Pro Glu Glu Lys Cys Gln Ala Tyr Glu Ser Asn Arg
    120             125             130

GAA TCC CTT TTA AAT CAC TTT TTA TAT GAA GTT GCC AGA AGG AAC CCA
Glu Ser Leu Leu Asn His Phe Leu Tyr Glu Val Ala Arg Arg Asn Pro
135             140             145             150

TTT GTC TTC GCC CCT ACA CTT CTA ACT GTT GCT GTT CAT TTT GAG GAG
```

FIG. 4B

|     |     |     |     |     |     |     |     |     |     |     |     |     |
| --- | --- | --- | --- | --- | --- | --- | --- | --- | --- | --- | --- | --- |
| Phe | Val | Phe | Ala | Pro<br>155 | Thr | Leu | Leu | Thr | Val<br>160 | Ala | Val | His | Phe | Glu<br>165 | Glu |

```
GTG GCC AAA TCA TGT TGT GAA GAA CAA AAC AAA GTC AAC TGC CTT CAA
Val Ala Lys Ser Cys Cys Glu Glu Gln Asn Lys Val Asn Cys Leu Gln
        170             175                 180

ACA AGG GCA ATA CCT GTC ACA CAA TAT TTA AAA GCA TTT TCT TCT TAT
Thr Arg Ala Ile Pro Val Thr Gln Tyr Leu Lys Ala Phe Ser Ser Tyr
        185             190                 195

CAA AAA CAT GTC TGT GGG GCA CTT TTG AAA TTT GGA ACC AAA GTT GTA
Gln Lys His Val Cys Gly Ala Leu Leu Lys Phe Gly Thr Lys Val Val
    200             205                 210

CAC TTT ATA TAT ATT GCG ATA CTC AGT CAA AAA TTC CCC AAG ATT GAA
His Phe Ile Tyr Ile Ala Ile Leu Ser Gln Lys Phe Pro Lys Ile Glu
215             220                 225                 230

TTT AAG GAG CTT ATT TCT CTT GTA GAA GAT GTT TCT TCC AAC TAT GAT
Phe Lys Glu Leu Ile Ser Leu Val Glu Asp Val Ser Ser Asn Tyr Asp
            235                 240                 245

GGA TGC TGT GAA GGG GAT GTT GTG CAG TGC ATC CGT GAC ACG AGC AAG
Gly Cys Cys Glu Gly Asp Val Val Gln Cys Ile Arg Asp Thr Ser Lys
            250                 255             260

GTT ATG AAC CAT ATT TGT TCA AAA CAA GAT TCT ATC TCC AGC AAA ATC
Val Met Asn His Ile Cys Ser Lys Gln Asp Ser Ile Ser Ser Lys Ile
        265                 270                 275

AAA GAG TGC TGT GAA AAG AAA ATA CCA GAG CGC GGC CAG TGC ATA ATT
Lys Glu Cys Cys Glu Lys Lys Ile Pro Glu Arg Gly Gln Cys Ile Ile
    280                 285                 290

AAC TCA AAC AAA GAT GAT AGA CCA AAG GAT TTA TCT CTA AGA GAA GGA
Asn Ser Asn Lys Asp Asp Arg Pro Lys Asp Leu Ser Leu Arg Glu Gly
295             300                 305                 310

AAA TTT ACT GAC AGT GAA AAT GTG TGT CAA GAA CGA GAT GCT GAC CCA
Lys Phe Thr Asp Ser Glu Asn Val Cys Gln Glu Arg Asp Ala Asp Pro
            315                 320                 325

GAC ACC TTC TTT GCG AAG TTT ACT TTT GAA TAC TCA AGG AGA CAT CCA
Asp Thr Phe Phe Ala Lys Phe Thr Phe Glu Tyr Ser Arg Arg His Pro
        330                 335                 340

GAC CTG TCT ATA CCA GAG CTT TTA AGA ATT GTT CAA ATA TAC AAA GAT
Asp Leu Ser Ile Pro Glu Leu Leu Arg Ile Val Gln Ile Tyr Lys Asp
        345             350                 355

CTC CTG AGA AAT TGC TGC AAC ACA GAA AAC CCT CCA GGT TGT TAC CGT
Leu Leu Arg Asn Cys Cys Asn Thr Glu Asn Pro Pro Gly Cys Tyr Arg
360                 365                 370

TAC GCG GAA GAC AAA TTC AAT GAG ACA ACT GAG AAA AGC CTC AAG ATG
Tyr Ala Glu Asp Lys Phe Asn Glu Thr Thr Glu Lys Ser Leu Lys Met
375                 380                 385                 390
```

FIG. 4C

```
GTA CAA CAA GAA TGT AAA CAT TTC CAG AAT TTG GGG AAG GAT GGT TTG
Val Gln Gln Glu Cys Lys His Phe Gln Asn Leu Gly Lys Asp Gly Leu
                395             400                 405

AAA TAC CAT TAC CTC ATC AGG CTC ACG AAG ATA GCT CCC CAA CTC TCC
Lys Tyr His Tyr Leu Ile Arg Leu Thr Lys Ile Ala Pro Gln Leu Ser
            410             415                 420

ACT GAA GAA CTG GTG TCT CTT GGC GAG AAA ATG GTG ACA GCT TTC ACT
Thr Glu Glu Leu Val Ser Leu Gly Glu Lys Met Val Thr Ala Phe Thr
        425             430                 435

ACT TGC TGT ACG CTA AGT GAA GAG TTT GCC TGT GTT GAT AAT TTG GCA
Thr Cys Cys Thr Leu Ser Glu Glu Phe Ala Cys Val Asp Asn Leu Ala
    440             445                 450

GAT TTA GTT TTT GGA GAG TTA TGT GGA GTA AAT GAA AAT CGA ACT ATC
Asp Leu Val Phe Gly Glu Leu Cys Gly Val Asn Glu Asn Arg Thr Ile
455         460                 465                     470

AAC CCT GCT GTG GAC CAC TGC TGT AAA ACA AAC TTT GCC TTC AGA AGG
Asn Pro Ala Val Asp His Cys Cys Lys Thr Asn Phe Ala Phe Arg Arg
                475             480                 485

CCC TGC TTT GAG AGT TTG AAA GCT GAT AAA ACA TAT GTG CCT CCA CCT
Pro Cys Phe Glu Ser Leu Lys Ala Asp Lys Thr Tyr Val Pro Pro Pro
            490             495                 500

TTC TCT CAA GAT TTA TTT ACC TTT CAC GCA GAC ATG TGT CAA TCT CAG
Phe Ser Gln Asp Leu Phe Thr Phe His Ala Asp Met Cys Gln Ser Gln
        505             510                 515

AAT GAG GAG CTT CAG AGG AAG ACA GAC AGG TTT CTT GTC AAC TTA GTG
Asn Glu Glu Leu Gln Arg Lys Thr Asp Arg Phe Leu Val Asn Leu Val
    520             525                 530

AAG CTG AAG CAT GAA CTC ACA GAT GAA GAG CTG CAG TCT TTG TTT ACA
Lys Leu Lys His Glu Leu Thr Asp Glu Glu Leu Gln Ser Leu Phe Thr
535             540             545                     550

AAT TTC GCA AAT GTA GTG GAT AAG TGC TGC AAA GCA GAG AGT CCT GAA
Asn Phe Ala Asn Val Val Asp Lys Cys Cys Lys Ala Glu Ser Pro Glu
                555             560                 565

GTC TGC TTT AAT GAA GAG AGT CCA AAA ATT GGC AAC TGAAGCCAGC
Val Cys Phe Asn Glu Glu Ser Pro Lys Ile Gly Asn
            570             575

TGCTGGAGAT ATGTAAAGAA AAAAGCACCA AAGGGAAGGC TTCCTATCTG TGTGGTGATG

AATCGCATTT CCTGAGAACA AAATAAAAGG ATTTTTCTGT AACTGTCACC TGAAATAATA

CATTGCAGCA AGCAATAAAC ACAACATTTT GTAAAGTTAA AAA
```

TISSUE SPECIFIC TRANSGENE EXPRESSION

This application is a continuation-in-part of U.S. Ser. No. 08/141,322 filed Oct. 18, 1993, now abandoned.

BACKGROUND

1. Field of the Invention

This invention relates to the field of recombinant DNA technology, especially to nucleic acid sequences useful for constructing a transgenic mammal. More specifically, the invention concerns expression of a transgene in certain tissues or organs of a mammal.

2. Description of Related Art

1. Tissue Specific Expression

Production of a transgenic mammal involves the insertion of a nucleic acid sequence, often called a transgene, which codes for a particular polypeptide, into one or more chromosomes of the mammal. This is typically accomplished by inserting the transgene into the pronucleus of an isolated mammalian egg. The transgene becomes incorporated into the DNA of the developing embryo. This embryo is then implanted into a surrogate host for the duration of gestation. The offspring of the surrogate host are evaluated for the presence of the transgene.

Expression of the transgene, i.e., production of the protein encoded by the transgene nucleic acid sequence, may confer a new phenotype on the mammal. Depending on the transgene(s) inserted into the animal and the level of expression of the transgene in the mammal, the mammal may become more or less susceptible to a particular disease or series of diseases. Such transgenic mammals are valuable for in vivo screening and testing of compounds that may be useful in treating or preventing the disease(s), and/or for developing methods useful in diagnosing the disease.

While methods for insertion of a novel gene into a mammal have developed rapidly, several problems with the application of this technology remain. One such problem concerns limiting expression of the gene primarily to a selected tissue or tissues where expression is desired.

Enhanced and/or specific expression of a gene in a select tissue or tissues of a mammal is complex. Expression of a gene is typically regulated at least in part by a non-coding nucleic acid sequence termed a promoter. The promoter is often located near or adjacent to the nucleic acid sequence encoding the polypeptide to be expressed. Frequently, the activity of a promoter is in turn regulated by other nucleic acid sequences termed enhancers and suppressors (also known as silencers). Enhancers increase the level of expression of the gene while suppressors or silencers decrease expression. The location of enhancers and suppressors along a nucleic acid sequence with respect to the promoter and coding sequence is quite varied for different genes. Enhancers and suppressors may be located near or adjacent to the promoter, i.e., within about 1 kilobase (kb) along a strand of DNA (chromosome or vector), or may be located at a much greater distance, e.g., up to 50 kb or more away from the promoter on a chromosome and still exert an effect on the activity of the promoter. Further, they may be located upstream (i.e., 5' to the promoter and coding sequence), or downstream (3' to the promoter and coding sequence). Such positioning for promoter activity is a function of both the type of promoter and the type of enhancer or suppressor used. To further complicate the regulation, enhancers and suppressors may exert their effect on the promoter of more than one gene within a chromosomal locus.

Several enhancers and suppressors have been identified. For example, the level of expression of the gene encoding transthyretin is affected by an enhancer element located about 2 kb upstream from the promoter (Yan et al., *EMBO J.*, 9:869-AFM8 [1990]). Liver specific expression of the albumin gene is regulated by an enhancer located about 10 kb upstream of its promoter (Hammer et al., *Science*, 235:53–58 [1987]). Tissue specific regulation of the alpha-fetoprotein gene involves three enhancer elements located 1 to 7 kb upstream of the transcription start site of the gene (Pinkert et al., *Genes & Dev.*, 1:268–276 [1987]).

Another enhancer is the hepatocyte-specific control region, or "HCR". The human HCR is believed to be about 774 base pairs (bp) in size or less (Simonet et al., *J. Biol. Chem.*, 268: 8221–8229 [1993]), but has recently been reported to be at least somewhat active as a 150 to 154 bp fragment (Breslow, *Proc. Natl. Acad. Sci. USA*, 90:8314–8318 [1993]; Shacter et al., *J. Lipid Res.*, 34:1699–1707 [1993]). The HCR is located on chromosome 19, about 18 kilobases (kb) downstream of the apolipoprotein E (apoE) promoter/gene sequence, about 9 kilobases downstream of the apolipoprotein C-I (apoC-I) promoter/gene sequence, and about 2 kilobases (kb) upstream of the apolipoprotein C-I (apoC-I') pseudogene sequence (Simonet et al., [1993], supra; Simonet et al., *J. Biol. Chem.*, 266:8651–8654 [1991]; Simonet et al., *J. Biol. Chem.*, 265:10809–10812 [1990]; Taylor et al., *Current Opinion in Lipidol.*, 2:73–80 [1991]). The HCR appears to be important in expression of the genes ApoE and ApoC-I in the liver; in its absence, these genes are not expressed at detectable levels in this tissue (Simonet et al. [1993], supra).

The effect of the HCR on a heterologous promoter has been evaluated in transgenic mice. The apolipoprotein A-IV promoter and coding sequence were ligated to a 1.7 kb nucleic acid sequence containing the HCR. Transgenic mice containing this construct had high levels of expression of apolipoprotein A-IV in the liver (Simonet et al., supra).

2. Interleukin-8

The interleukins are a group of naturally occurring proteins that act as chemical mediators of the differentiation processes for red and white blood cells. One of the interleukins, IL-8 (also known as Neutrophil Activating Peptide-1, or NAP-1), has been shown to be a neutrophil chemoattractant with the ability to activate neutrophils and stimulate the respiratory burst (Colditz et al., *J. Leukocyte Biol.*, 48:129–137 [1990]; Leonard et al., *J. Invest. Derm.*, 96:690–694 [1991]). IL-8 has been termed a proinflammatory cytokine due to its involvement in neutrophil recruitment to sites of acute and chronic inflammation.

Zwahlen et al. (*Int. Rev. Exp. Path.*, 34B:22–42 [1993]) describe some effects of IL-8 injected into some rodents. When injected intradermally into rats, IL-8 induced neutrophil infiltration at the site of injection. Intravenous injection of IL-8 into rabbits resulted in neutrophil sequestration in the lungs.

Vogels et al. (*Antimicrobial Agents and Chemotherapy*, 37:276–280 [1993]) describe the effect of administering IL-8 to mice either before or after infection of the mice with three different pathogens. Under certain conditions, administration of IL-8 was shown to have a detrimental effect on the survival of the mice.

Van Zee et al. (*J. Immunol.*, 148:1746–1752 [1992]) describe administration of IL-8 to baboons. The animals developed neutropenia rapidly after IL-8 administration. This neutropenia is transient and is followed by a marked granulocytosis which persists for as long as IL-8 is present in the circulation.

Burrows et al. (*Ann. NY Acad. Sci.*, 629:422–424 [1991]) show that guinea pigs injected with IL-8 had a higher level of T-lymphocyte and eosinophil accumulation in the lung than did control animals.

3. Keratinocyte Growth Factor

Keratinocyte growth factor (KGF) is a mitogen that has been identified as specific for epithelial cells, especially keratinocytes (Rubin et al., *Proc. Natl. Acad. Sci. USA*, 86:802–806 [1989]; Finch et al., *Science*, 245:752–755 [1990]; Marchese et al., *J. Cell Physiol.*, 144:326–332 [1990]). KGF has shown potential for repair of epidermal tissues such as the skin, and epithelial tissues of the digestive tract. The DNA encoding KGF has been cloned and sequenced (PCT 90/08771, published Aug. 9, 1990).

Guo et al. (*EMBO J.*, 12:973–986 [1993]) have prepared a transgenic mouse containing a transgene constructed of the human keratin 14 promoter and the human keratinocyte growth factor gene. The mouse showed a number of phenotypic differences as compared with non-transgenics such as wrinkled skin and reduced hair follicle density.

4. Monocyte Chemoattractant Protein

Monocyte chemoattractant protein (also known as MCP-1) is a protein that is produced by activated leukocytes in response to certain stimuli. The gene encoding human MCP-1 has been cloned and sequenced (Furutani et al., *Biochem. Biophys. Res. Comm.*, 159:249–255 [1989]; Yoshimura et al., Chemotactic Cytokines, Westwood et al., eds. Plenum Press, NY [1991], pp.47–56). MCP-1 serves to attract monocytes to the site of its release, and is believed to be involved in the cellular immune response and in acute tissue injury (Leonard et al., *Immunol. Today*, 11:97–101 [1990]). MCP-1 has been shown to be produced by some tumor cells in vitro, and in human metastatic melanomas in vivo (Graves et al., *Am J. Pathol.*, 140:9–14 [1992]).

5. Human Afamin

Afamin ("AFM") is a novel protein recently identified in human serum. AFM has a molecular weight of about 87,000 daltons when run on SDS_PAGE, and shares significant homology to members of the albumin family of proteins including vitamin D binding protein (VDB), alpha fetoprotein, and albumin. In addition, AFM has the characteristic pattern of disulfide bonds observed in this family. AFM cDNA has been stably transfected into Chinese hamster ovary cells, and recombinant AFM (rAFM) has been purified from the conditioned culture medium of these cells. Both AFM and rAFM react with a polyclonal antibody that was raised against a synthetic peptide derived from the deduced amino acid sequence of AFM. There is a need in the art to provide in vivo systems for evaluating the effects of one or more genes on certain diseases.

Accordingly, it is an object of this invention to provide a mammal containing a nucleic acid construct comprising a transgene, and expressing the transgene, where the mammal may be used as an in vivo system to analyze the course of a disease.

It is a further objective to provide a transgene nucleic acid construct and an expression vector that enhance tissue specific expression of a transgene in liver tissue of a transgenic mammal.

Other such objects will readily be apparent to one of ordinary skill in the art.

SUMMARY OF THE INVENTION

In one aspect, the present invention provides a nucleic acid sequence comprising an HCR enhancer operably linked to a promoter and a transgene. The promoter may be selected from the group of promoters consisting of: ApoA-I, ApoA-II, ApoA-III, ApoA-IV, ApoB-48, ApoB-100, ApoC-I, ApoC-II, ApoC-III, ApoE, albumin, alpha feto protein, PEPCK, transthyretin, SV40, CMV, and TK. The transgene may be selected from the group consisting of: interleukin 1, interleukin 2, interleukin 3, interleukin 4, interleukin 5, interleukin 6, interleukin 7, interleukin 8, interleukin 9, interleukin 10, interleukin 11, interleukin 12, ENA-78, interferon-α, interferon-β, interferon-γ, granulocyte-colony stimulating factor, granulocyte-macrophage colony simulating factor, macrophage colony stimulating factor, stem cell factor, keratinocyte growth factor, MCPI, AFM, and TNF, and fragments thereof.

In one other aspect, the invention provides a non-human mammal and its progeny containing a nucleic acid sequence comprising an HCR enhancer operably linked to a promoter and a transgene.

The invention further provides a non-human transgenic mammal containing nucleic acid sequence comprising an HCR enhancer, the human ApoE promoter, the human ApoE intron 1 linked at its 5' end to the human ApoE exon 1 and at its 3' end to a portion of the human ApoE exon 2, and at least a portion of the coding sequence of the transgene human IL-8, the transgene KGF, or the transgene AFM.

BRIEF DESCRIPTION OF THE DRAWINGS

FIG. 1 depicts the nucleic acid sequence of the 774 base pair human HCR (SEQ ID NO: 1). This sequence was derived from the vector pCI-CI'PX#8, deposited with the American Type Culture Collection (ATCC).

FIG. 3 depicts the level of IL-8 and circulating neutrophils in both control and transgenic mice.

FIGS. 4A–C depicts a nucleic acid molecule (cDNA) of approximately 2.3 kb encoding human AFM (SEQ ID NO:23). The translated amino acid sequence of AFM is also shown (SEQ ID NO:24). The amino acid positions are numbered, with −21 through −1 being the signal peptide sequence, and 1–578 being the mature protein sequence.

DETAILED DESCRIPTION OF THE INVENTION

Definitions

Figure 2A:
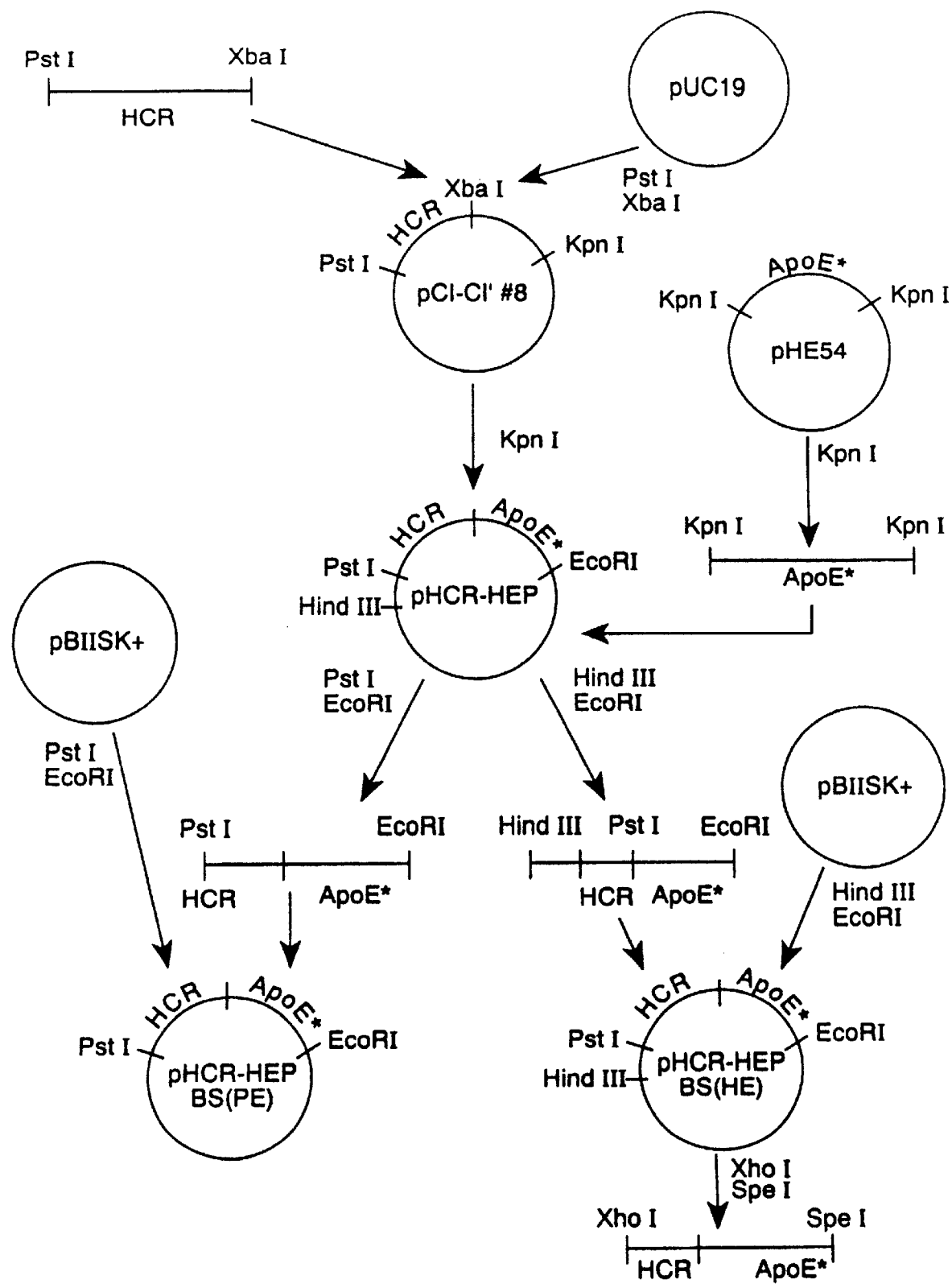
FIGS. 2A–C depict the transgene construct used to generate IL-8, KGF, and MCP-1 transgenic mice. Vectors are labeled as referenced in the Examples. Selected restriction enzymes are shown. "ApoE*" refers to the ApoE promoter, first exon, first intron and a portion of the second intron; "SV40PA" refers to the SV40 polyA+sequence, as described in the Examples.

The term "operably linked" refers to the arrangement of various nucleic acid molecule elements relative to each such that the elements are functionally connected and are able to interact with each other. Such elements may include, without limitation, a promoter, an enhancer, a polyadenylation sequence, one or more introns and/or exons, and a coding sequence of a gene of interest to be expressed (i.e., the transgene). The nucleic acid sequence elements, when properly oriented or operably linked, act together to modulate the activity of one another, and ultimately may affect the level of expression of the transgene. By modulate is meant increasing, decreasing, or maintaining the level of activity of a particular element. The position of each element relative to other elements may be expressed in terms of the 5' terminus and the 3' terminus of each element, and the distance between any particular elements may be referenced by the number of intervening nucleotides, or base pairs, between the elements.

The term "transgene" refers to a particular nucleic acid sequence encoding a polypeptide or a portion of a polypeptide to be expressed in a cell into which the nucleic acid sequence is inserted. The term "transgene" is meant to include (1) a nucleic acid sequence that is not naturally found in the cell (i.e., a heterologous nucleic acid sequence); (2) a nucleic acid sequence that is a mutant form of a nucleic acid sequence naturally found in the cell into which it has been inserted; (3) a nucleic acid sequence that serves to add additional copies of the same (i.e., homologous) or a similar nucleic acid sequence naturally occurring in the cell into which it has been inserted; or (4) a silent naturally occurring or homologous nucleic acid sequence whose expression is induced in the cell into which it has been inserted. By "mutant form" is meant a nucleic acid sequence that contains one or more nucleotides that are different from the wild-type or naturally occurring sequence, i.e., the mutant nucleic acid sequence contains one or more nucleotide substitutions, deletions, and/or insertions. In some cases, the transgene may also include a sequence encoding a leader peptide or signal sequence such that the transgene product will be secreted from the cell.

The term "promoter" refers to a nucleic acid sequence that regulates, either directly or indirectly, the transcription of a corresponding nucleic acid coding sequence to which it is operably linked. The promoter may function alone to regulate transcription, or, in some cases, may act in concert with one or more other regulatory sequences such as an enhancer or silencer to regulate transcription of the transgene.

The term "an HCR enhancer" refers to a non-coding nucleic acid sequence naturally located on human chromosome 19 within or proximal to the apoE/apoC-I gene locus, downstream of the ApoE and ApoC-I promoter/gene sequences, but upstream of the ApoC-I pseudogene sequence. As used herein, an HCR enhancer refers to any nucleic acid sequence of about 774 base pairs, and to fragment(s) thereof that has (have) biological activity. When an HCR enhancer is operably linked to both a promoter and a transgene, the HCR enhancer can (1) confer a significant degree of liver specific expression of the transgene, and/or (2) can increase the level of expression of the transgene in the liver.

The term "rodent" refers to all members of the phylogenetic order Rodentia, such as, for example, mouse, rat, hamster, squirrel, or beaver.

The term "progeny" refers to all offspring of the transgenic mammal, and-includes every generation subsequent to the originally transformed transgenic mammal.

PREPARATION OF THE INVENTION

1. Preparation of DNA Constructs

A. Selection of Transgene

This invention contemplates expression of one or more transgenes primarily in the liver and/or the gastro-intestinal tissue of a transgenic mammal. Where the transgene is expressed primarily in the liver, the gene product may be secreted into the bloodstream after synthesis. Thus, included within the scope of this invention is any transgene encoding a polypeptide to be circulated in the blood. Typically, the transgene will be a nucleic acid molecule encoding a polypeptide involved in the immune response, hematopoiesis, inflammation, cell growth and proliferation, cell lineage differentiation, and/or the stress response. The transgene may be homologous or heterologous to the promoter and/or to the mammal. In addition, the transgene may be a full length cDNA or genomic DNA sequence, or any fragment, subunit or mutant thereof that has at least some biological activity. Optionally, the transgene may be a hybrid nucleic acid sequence, i.e., one constructed from homologous and/or heterologous cDNA and/or genomic DNA fragments. The transgene may also optionally be a mutant of one or more naturally occurring cDNA and/or genomic sequences.

The transgene may be isolated and obtained in suitable quantity using one or more methods that are well known in the art. These methods and others useful for isolating a transgene are set forth, for example, in Sambrook et al. (*Molecular Cloning: A Laboratory Manual*, Cold Spring Harbor Laboratory Press, Cold Spring Harbor, N.Y. [1989]) and in Berger and Kimmel (*Methods in Enzymology: Guide to Molecular Cloning Techniques*, vol. 152, Academic Press, Inc., San Diego, Calif. [19AFM]).

Where the nucleic acid sequence of the transgene is known, the transgene may be synthesized, in whole or in part, using chemical synthesis methods such as those described in Engels et al. (*Angew. Chem. Int. Ed. Engl.*, 28:716–734 [1989]). These methods include, inter alia, the phosphotriester, phosphoramidite and H-phosphonate methods of nucleic acid synthesis.

Alternatively, the transgene may be obtained by screening an appropriate cDNA or genomic library using one or more nucleic acid probes (oligonucleotides, cDNA or genomic DNA fragments with an acceptable level of homology to the transgene to be cloned, and the like) that will hybridize selectively with the transgene DNA.

Another suitable method for obtaining a transgene is the polymerase chain reaction (PCR). However, successful use of this method requires that enough information about the nucleic acid sequence of the transgene is known so as to design suitable oligonucleotide primers useful for amplification of the appropriate nucleic acid sequence.

Where the method of choice requires the use of oligonucleotide primers or probes (e.g. PCR, cDNA or genomic library screening), the oligonucleotide sequences selected as probes or primers should be of adequate length and sufficiently unambiguous so as to minimize the amount of non-specific binding that will occur during library screening or PCR. The actual sequence of the probes or primers is usually based on conserved or highly homologous sequences or regions from the same or a similar gene from another organism. Optionally, the probes or primers can be degenerate.

In cases where only the amino acid sequence of the transgene is known, a probable and functional nucleic acid sequence may be inferred for the transgene using known and preferred codons for each amino acid residue. This sequence can then be chemically synthesized.

This invention contemplates the use of transgene mutant sequences. A mutant transgene is a transgene containing one or more nucleotide substitutions, deletions, and/or insertions as compared to the wild type sequence. The nucleotide substitution, deletion, and/or insertion can give rise to a gene product (i.e., protein) that is different in its amino acid sequence from the wild type amino acid sequence. Preparation of such mutants is well known in the art, and is described for example in Wells et al. (*Gene*, 34:315 [1985]), and in Sambrook et al, supra.

Preferred transgenes of the present invention are erythropoietin (EPO), interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), ENA-78 (Walz et al., *J. Exp. Med.*, 174:1355–1362 [1991]; Strieter et al., *Immunol. Invest.*, 21:589–596 [1992]), interferon-α, interferon-β, interferon-γ, granulocyte-colony stimulating factor (G-CSF), granulocyte-macrophage colony stimulating factor (GM-CSF), macrophage colony stimulating factor (M-CSF), stem cell factor (SCF), keratinocyte growth factor (KGF), monocyte chemoattractant protein-1 (MCP-1; Furutani et al., supra), tumor necrosis factor (TNF), AFM, and fragments, subunits or mutants thereof. More preferred transgenes include erythropoietin, interleukin 8, MCP-1, keratinocyte growth factor, AFM, and ENA-78. The most preferred transgenes include human interleukin 8, human keratinocyte growth factor, AFM, and MCP-1.

B. Selection of Regulatory Elements

This invention contemplates the use of promoters that are regulated at least in part by an HCR enhancer which results in increased liver expression of the transgene.

The promoter may be homologous (i.e., from the same species as the mammal to be transfected with the transgene) or heterologous (i.e., from a source other than the species of the mammal to be transfected with the transgene). As such, the source of the promoter may be any unicellular prokaryotic or eukaryotic organism, any vertebrate or invertebrate organism, or any plant, provided that the promoter is functional in combination with an HCR enhancer. The more preferred promoters of this invention are the ApoA-I promoter, the ApoA-II promoter, the ApoA-IV promoter, the ApoB promoter, the ApoC-I promoter, the ApoC-II promoter, the ApoC-III promoter, the ApoE promoter, the albumin promoter, the alpha feto protein promoter, the PEPCK (phosphoenol pyruvate carboxykinase) promoter (EP 365,591, published May 2, 1990), the transthyretin promoter, the SV40 promoter, the CMV promoter, and the TK (thymidine kinase) promoter. The most preferred promoters of this group are ApoE, ApoC-I, and ApoA-IV. The most preferred promoters are human ApoE and human ApoC-I.

The preferred HCR enhancer element contemplated herein is a non-coding DNA sequence located on human chromosome 19 within, or proximal to, the apoE/apoC-I gene locus, downstream of the ApoE and ApoC-I genes, but upstream of the ApoC-I pseudogene. The approximately 774 base pair HCR has been deposited under the Budapest Treaty with the American Type Culture Collection (ATCC; 12301 Parklawn Drive, Rockville, Md. 20852) as accession number 69422. The date of deposit is Sep. 17, 1993. Fragments of this HCR sequence are also contemplated herein, provided that the fragment has the property of modulating expression of a transgene in the liver (i.e., is biologically active).

The promoter sequences of this invention may be obtained by any of several methods well known in the art. Typically, promoters useful herein will have been previously identified by mapping and/or by restriction endonuclease digestion and can thus be isolated from the proper tissue source using the appropriate restriction endonucleases. In some cases, the promoter may have been sequenced. For those promoters whose DNA sequence is known, the promoter may be synthesized using the methods described above for transgene synthesis.

Where all or only portions of the promoter sequence are known, the promoter may be obtained using PCR and/or by screening a genomic library with suitable oligonucleotide and/or promoter sequence fragments from the same or another species.

Where the promoter sequence is not known, a fragment of DNA containing the promoter may be isolated from a larger piece of DNA that may contain, for example, a coding sequence or even another gene or genes. Isolation may be accomplished by restriction endonuclease digestion using one or more carefully selected enzymes to isolate the proper DNA fragment. After digestion, the desired fragment is isolated by agarose gel purification, Qiagen column or other methods known to the skilled artisan. Selection of suitable enzymes to accomplish this purpose will be readily apparent to one of ordinary skill in the art.

C. Selection of Other Vector Components

In addition to the transgene, the promoter, and the HCR enhancer, the vectors useful in this invention typically contain one or more other elements useful for (1) optimal functioning of the vector in the mammal into which the vector is transfected, and (2) amplification of the vector in bacterial or mammalian host cells. Each of these elements will be positioned appropriately in the vector with respect to each other element so as to maximize their respective activities. Such positioning is well known to the ordinary skilled artisan. The following elements may be optionally included in the vector as appropriate.

i. Signal Sequence Element

For those embodiments of the invention where the transgene is to be secreted, a signal sequence, is frequently present to direct the polypeptide encoded by the transgene out of the cell where it is synthesized. Typically, the signal sequence is positioned in the coding region of the transgene towards or at the 5' end of the coding region. Many signal sequences have been identified, and any of them that are functional in the transgenic tissue may be used in conjunction with the transgene. Therefore, the signal sequence may be homologous or heterologous to the transgene, and may be homologous or heterologous to the transgenic mammal. Additionally, the signal sequence may be chemically synthesized using methods set forth above. However, for purposes herein, preferred signal sequences are those that occur naturally with the transgene (i.e., are homologous to the transgene).

ii. Membrane Anchoring Domain Element

In some cases, it may be desirable to have a transgene expressed on the surface of a particular intracellular membrane or on the plasma membrane. Naturally occurring membrane proteins contain, as part of the translated polypeptide, a stretch of amino acids that serve to anchor the protein to the membrane. However, for proteins that are not naturally found on the membrane, such a stretch of amino acids may be added to confer this feature. Frequently, the anchor domain will be an internal portion of the protein and thus will be engineered internally into the transgene. However, in other cases, the anchor region may be attached to the 5' or 3' end of the transgene. Here, the anchor domain may first be placed into the vector in the appropriate position as a separate component from the transgene. As for the signal sequence, the anchor domain may be from any source and thus may be homologous or heterologous with respect to both the transgene and the transgenic mammal. Alternatively, the anchor domain may be chemically synthesized using methods set forth above.

iii. Origin of Replication Element

This component is typically a part of prokaryotic expression vectors purchased commercially, and aids in the amplification of the vector in a host cell. If the vector of choice does not contain an origin of replication site, one may be chemically synthesized based on a known sequence, and ligated into the vector.

iv. Transcription Termination Element

This element is typically located 3' to the transgene coding sequence and serves to terminate transcription of the transgene. Usually, the transcription termination element is a polyadenylation signal sequence. While the element is easily cloned from a library or even purchased commercially as part of a vector, it can also be readily synthesized using methods for nucleic acid synthesis such as those described above.

v. Intron Element

In many cases, transcription of the transgene is increased by the presence of one or more introns on the vector. The intron may be naturally occurring within the transgene sequence, especially where the transgene is a full length or a fragment of a genomic DNA sequence. Where the intron is not naturally occurring within the DNA sequence (as for most cDNAs), the intron(s) may be obtained from another source. The intron may be homologous or heterologous to the transgene and/or to the transgenic mammal. The position of the intron with respect to the promoter and the transgene is important, as the intron must be transcribed to be effective. As such, where the transgene is a cDNA sequence, the preferred position for the intron is 3' to the transcription start site, and 5' to the polyA transcription termination sequence. Preferably for cDNA transgenes, the intron will be located on one side or the other (i.e., 5' or 3') of the transgene sequence such that it does not interrupt the transgene sequence. Any intron from any source, including any viral, prokaryotic and eukaryotic (plant or animal) organisms, may be used to practice this invention, provided that it is compatible with the host cell(s) into which it is inserted. Also included herein are synthetic introns. optionally, more than one intron may be used in the vector. A preferred intron is intron 1 of the human ApoE gene.

vi. Selectable Marker(s) Element

Selectable marker genes encode proteins necessary for the survival and growth of transfected cells grown in a selective culture medium. Typical selection marker genes encode proteins that (a) confer resistance to antibiotics or other toxins, e.g., ampicillin, tetracycline, or kanomycin for prokaryotic host cells, and neomycin, hygromycin, or methotrexate for mammalian cells; (b) complement auxotrophic deficiencies of the cell; or (c) supply critical nutrients not available from complex media, e.g., the gene encoding D-alanine racemase for cultures of Bacilli.

All of the elements set forth above, as well as others useful in this invention, are well known to the skilled artisan and are described, for example, in Sambrook et al. (*Molecular Cloning: A Laboratory Manual*, Cold Spring Harbor Laboratory Press, Cold Spring Harbor, N.Y. [1989]) and Berger et al., eds. (*Guide to Molecular Cloning Techniques*, Academic Press, Inc., San Diego, Calif. [19AFM]).

D. Construction of Vectors

The vectors most useful in practicing this invention are those that are compatible with prokaryotic cell hosts. However, eukaryotic cell hosts, and vectors compatible with these cells, are within the scope of the invention.

In certain cases, some of the various vector elements may be already present in commercially available vectors such as pUC18, pUC19, pBR322, the pGEM vectors (Promega Corp, Madison, Wis.), the pBluescript® vectors such as pBIISK+/− (Stratagene Corp., La Jolla, Calif.), and the like, all of which are suitable for prokaryotic cell hosts.

However, where one or more of the elements are not already present in the vector to be used, they may be individually obtained and ligated into the vector. Methods used for obtaining each of the elements are well known to the skilled artisan and are comparable to the methods set forth above for obtaining a transgene (i.e., synthesis of the DNA, library screening, and the like).

Preferred vectors of this invention are the pGEM and the pBluescript®vectors. The most preferred vector is PBIISK+.

Vectors used for amplification of the transgene and/or for transfection of the mammalian embryos are constructed using methods well known in the art. Such methods include, for example, the standard techniques of restriction endonuclease digestion, ligation, agarose and acrylamide gel purification of DNA and/or RNA, column chromatography purification of DNA and/or RNA, phenol/chloroform extraction of DNA, DNA sequencing, polymerase chain reaction amplification, and the like, as set forth in Sambrook et al., supra.

The final vector used to practice this invention is typically constructed from a starting vector such as a commercially available vector. This vector may or may not contain some of the elements to be included in the completed vector. If none of the desired elements are present in the starting vector, each element may be individually ligated into the vector by cutting the vector with the appropriate restriction endonuclease(s) such that the ends of the element to be ligated in and the ends of the vector are compatible for ligation. In some cases, it may be necessary to "blunt" the ends to be ligated together in order to obtain a satisfactory ligation. Blunting is accomplished by first filling in "sticky ends" using Klenow DNA polymerase or T4 DNA polymerase in the presence of all four nucleotides. This procedure is well known in the art and is described for example in Sambrook et al., supra.

Alternatively, two or more of the elements to be inserted into the vector may first be ligated together (if they are to be positioned adjacent to each other) and then ligated into the vector.

One other method for constructing the vector to conduct all ligations of the various elements simultaneously in one reaction mixture. Here, many nonsense or nonfunctional vectors will be generated due to improper ligation or insertion of the elements, however the functional vector may be identified and selected by restriction endonuclease digestion.

After the vector has been constructed, it may be transfected into a prokaryotic host cell for amplification. Cells typically used for amplification are *E coli* DH5-alpha (Gibco/BRL, Grand Island, N.Y.) and other *E. coli* strains with characteristics similar to DH5-alpha.

Where mammalian host cells are used, cell lines such as Chinese hamster ovary (CHO cells; Urlab et al., *Proc. Natl. Acad. Sci USA*, 77:4216 [1980])) and human embryonic kidney cell line 293 (Graham et al., *J. Gen. Virol.*, 36:59 [1977]), as well as other lines, are suitable.

Transfection of the vector into the selected host cell line accomplished using such methods as calcium phosphate, electroporation, microinjection, lipofection or DEAE-dextran method. The method selected will in part be a function of the type of host cell to be transfected. These methods and other suitable methods are well known to the skilled artisan, and are set forth in Sambrook et al., supra.

After culturing the cells long enough for the vector to be sufficiently amplified (usually overnight for *E. coli* cells), the vector (often termed plasmid at this stage) is isolated from the cells and purified. Typically, the cells are lysed and the plasmid is extracted from other cell contents. Methods suitable for plasmid purification include inter alia, the alkaline lysis mini-prep method (Sambrook et al., supra).

E. Preparation of Plasmid for Insertion into the Embryo

Typically, the plasmid containing the transgene is linearized using a selected restriction endonuclease prior to insertion into the embryo. In some cases, it may be preferable to isolate the transgene, promoter, and regulatory elements as a linear fragment from the other portions of the vector, thereby injecting only a linear nucleic acid sequence containing the transgene, promoter, intron (if one is to be used), enhancer, polyA sequence, and optionally a signal sequence or membrane anchoring domain into the embryo. This may be accomplished by cutting the plasmid so as to remove the nucleic acid sequence region containing these elements, and purifying this region using agarose gel electrophoresis or other suitable purification methods.

2. Production of Transgenic Mammals

Transgenic mammals may be prepared using methods well known to the skilled artisan. For example, to prepare transgenic rodents such as mice, methods such as those set forth by Hogan et al., eds. (*Manipulating The Mouse Embryo: A Laboratory Manual*, Cold Spring Harbor Laboratory Press, Cold Spring Harbor, N.Y. [1986]) may be employed.

The specific line(s) of any mammalian species used to practice this invention are selected for general good health, good embryo yields, good pronuclear visibility in the embryos, and good reproductive fitness. For example, when transgenic mice are to be produced, lines such as C57/BL6× DBA2 F1 cross, or FVB lines are often used (obtained commercially from Charles River Labs, Boston, Mass.). The line(s) used to practice this invention may themselves be transgenics, and/or may be knockouts (i.e., mammals which have one or more genes partially or completely suppressed).

The age of the mammals that are used to obtain embryos and to serve as surrogate hosts is a function of the species used, but is readily determined by one of ordinary skill in the art. For example, when mice are used, pre-puberal females are preferred, as they yield more embryos and respond better to hormone injections.

Similarly, the male mammal to be used as a stud will normally be selected by age of sexual maturity, among other criteria.

Administration of hormones or other chemical compounds may be necessary to prepare the female for egg production, mating, and/or reimplantation of embryos. The type of hormones/cofactors and the quantity used, as well as the timing of administration of the hormones will vary for each species of mammal. Such considerations will be readily apparent to one of ordinary skill in the art.

Typically, a primed female (i.e., one that is producing eggs that can be fertilized) is mated with a stud male, and the resulting fertilized embryos are then removed for introduction of the transgene(s).

Alternatively, eggs and sperm may be obtained from suitable females and males and used for in vitro fertilization to produce an embryo suitable for introduction of the transgene.

Normally, fertilized embryos are incubated in suitable media until the pronuclei appear. At about this time, exogenous nucleic acid comprising the transgene of interest is introduced into the female or male pronucleus. In some species such as mice, the male pronucleus is preferred.

Introduction of nucleic acid may be accomplished by any means known in the art such as, for example, microinjection, electroporation, or lipofection. Following introduction of the transgene nucleic acid sequence into the embryo, the embryo may be incubated in vitro for varying amounts of time, or reimplanted into the surrogate host, or both. In vitro incubation to maturity is within the scope of this invention. One common method is to incubate the embryos in vitro for about 1–7 days, depending on the species, and then reimplant them into the surrogate host.

Reimplantation is accomplished using standard methods. Usually, the surrogate host is anesthetized, and the embryos are inserted into the oviduct. The number of embryos implanted into a particular host will vary by species, but will usually be comparable to the number of offspring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue (about 1 cm is removed from the tip of the tail) and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular markers or enzyme activities, and the like. Analysis of the blood may also be useful to detect the presence of the transgene product in the blood, as well as to evaluate the effect of the transgene on the levels of various types of blood cells and other blood constituents.

Progeny of the transgenic mammals may be obtained by mating the transgenic mammal with a suitable partner, or by in vitro fertilization of eggs and/or sperm obtained from the transgenic mammal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic mammals of this invention may be used to generate one or more cell lines. Such cell lines have many uses, as for example, to evaluate the effect(s) of the transgene on a particular tissue or organ, and to screen compounds that may affect the level of activity of the transgene in the tissue. Such compounds may be useful as therapeutics to modulate the activity of the transgene.

Production of cell lines may be accomplished using a variety of methods, known to the skilled artisan. The actual culturing conditions will depend on the tissue and type of cells to be cultured. Various media containing different concentrations of macro and micro nutrients, growth factors, serum, and the like, can be tested on the cells without undue experimentation to determine the optimal conditions for growth and proliferation of the cells. Similarly, other culturing conditions such as cell density, media temperature, and carbon dioxide concentrations in the incubator can also readily be evaluated.

The transformed mammals, their progeny, and transgenic cell lines of the present invention provide several important uses that will be readily apparent to one of ordinary skill in the art. The mammals and cell lines are particularly useful for (a) providing and evaluating the potential of treatments (such as gene therapy) for a variety of conditions and diseases, and/or (b) screening compounds that have potential as prophylactics or therapeutics. Such uses may be found for (1) conditions caused by inflammation, (2) immune system disorders, (3) epithelial cell repair (skin, lung and/or intestinal epithelia), (4) hematopoiesis, and/or (5) disorders caused by various physical and/or mental stresses. For example, transgenic mammals or cell lines containing the transgene for IL-8 will be useful for identifying compounds that modulate neutrophil migration; transgenic mammals containing the transgene KGF will be useful for evaluating epithelial tissue repair, and identifying compounds that affect this process.

In the case of transgenic mammals, screening of candidate compounds is conducted by administering the compound(s) to be tested to the mammal, over a range of doses, and evaluating the mammal's physiological response to the compound(s) over time. Administration may be by any appropriate means such as, for example, oral administration, or administration by injection, implantation, or transdermal delivery, depending on the chemical nature of the compound being evaluated. In some cases, it may be appropriate to administer the compound in conjunction with other compounds or co-factors that might enhance the efficacy of the compound.

In screening cell lines for compounds useful in treating the above mentioned problems, the compound is added to the cell culture medium at the appropriate time, and the cellular response to the compound is evaluated over time using the appropriate biochemical and/or histological assays. In some cases, it may be appropriate to apply the compound of interest to the culture medium in conjunction with other compounds or co-factors that might enhance the efficacy of the compound.

The invention will be more fully understood by reference to the following examples. They should not be construed in any way as limiting the scope of the present invention.

EXAMPLES

Example 1

Preparation of a HCR-IL-8 Transgenic Mouse

A. Construction of Transgene and Vectors

Figure 2B:
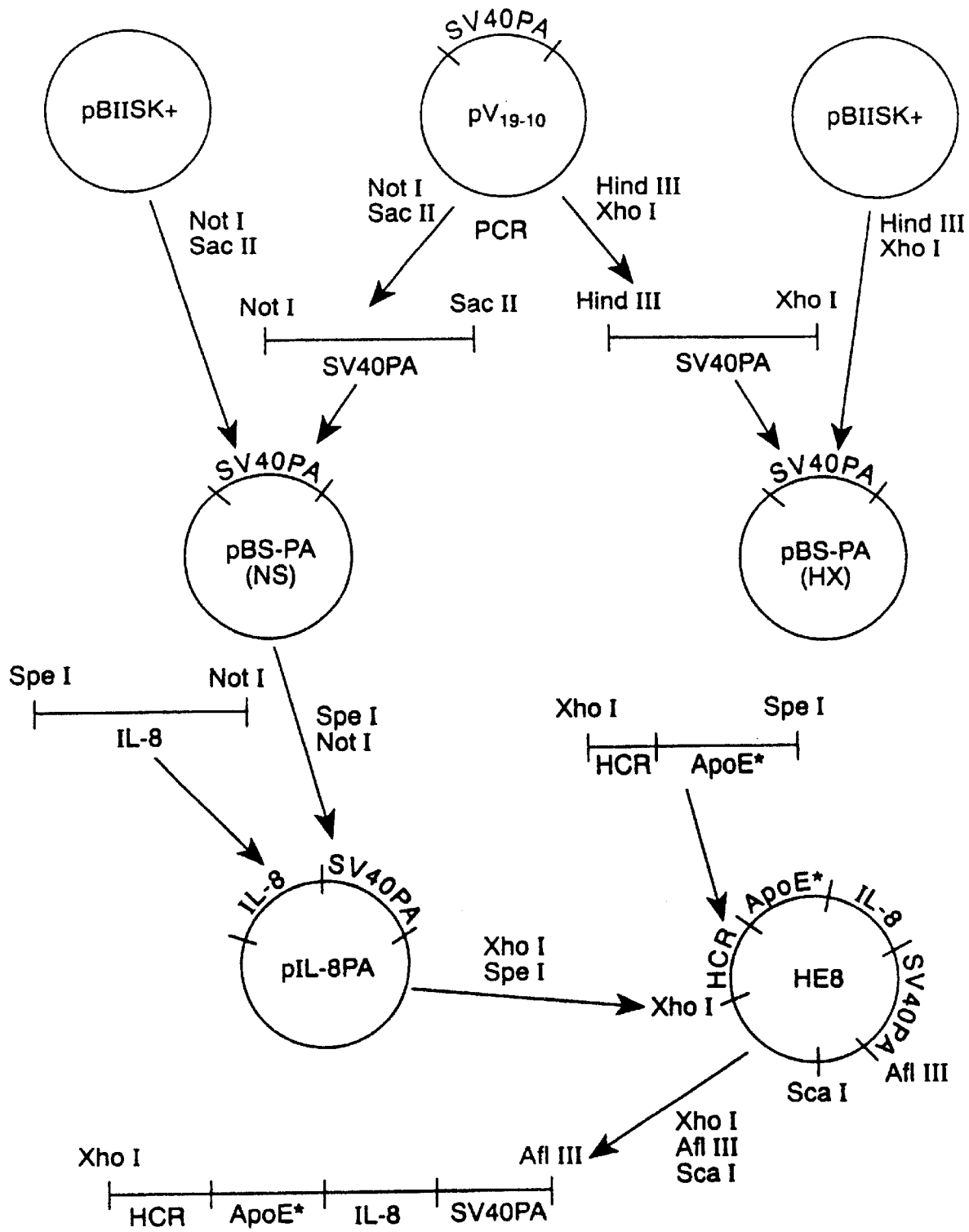
Figure 2C:
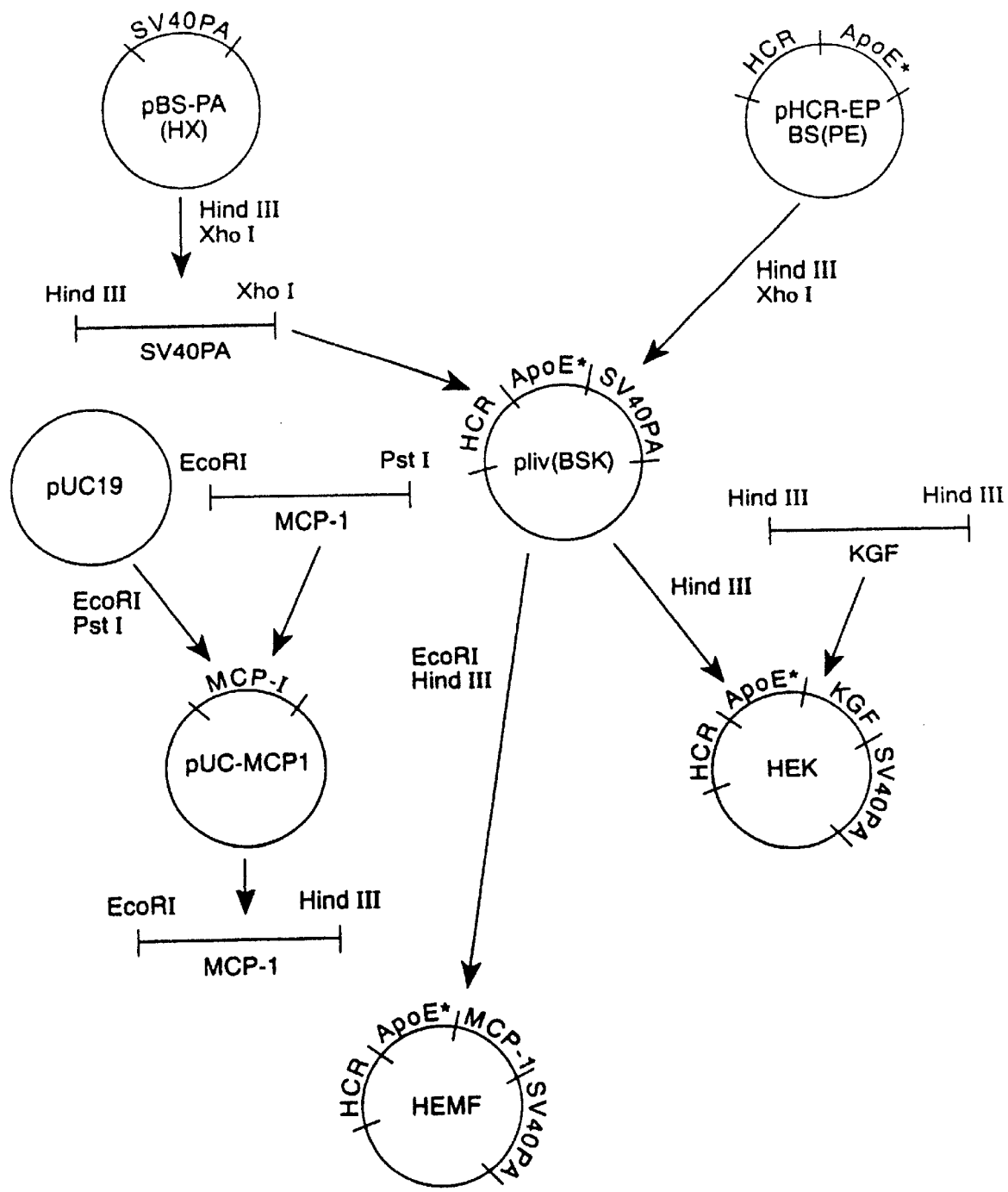

A diagram depicting the overall cloning strategy used herein is set forth in FIG. 2.

A PstI-XbaI DNA fragment of about 774 base pairs (containing HCR sequence) obtained from the human apoC-I/C-I' intergenic region on chromosome 19 (Simonet et al. [1993], supra) was subcloned into the PstI-XbaI sites of pUC19 (New England Biolabs, Beverly, Mass.). The resulting plasmid was designated pCI-CI'PX#8. This plasmid has been deposited on Sep. 17, 1993 with the ATCC as accession number 69422.

An approximately 1.45 kb Kpn-I fragment containing a contiguous piece of DNA consisting of 650 bp of the human ApoE gene 5'-flanking sequence, the first exon, first intron and a portion of the second exon of the ApoE gene was excised from the vector pHE54 (Simonet et al., [1993], supra). This fragment of about 1.45 kb was inserted by ligation into the Kpn-I cloning site of pCI-CI'PX#8. After ligation, the plasmid was transfected into E. coli strain DH5-alpha (Gibco/BRL, Grand Island, N.Y.). The cells were plated out on standard LB (Luria broth) or TB (Terrific broth) plus ampicillin medium (Sambrook et al., supra) on agarose plates, and grown up overnight at 37° C.

Colonies were then selected and grown up overnight in standard LB medium in the presence of ampicillin for amplification. After amplification, plasmid DNA from each amplified colony was prepared using the standard alkaline lysis miniprep method (Sambrook et al., supra), and the plasmid DNA was purified using a Qiagen column (Qiagen Corp., Chatsworth, Calif.). Purified plasmid was then digested with the restriction endonuclease BamHI and analyzed by agarose gel electrophoresis. Of 18 colonies analyzed, 6 were found to have a single insert ligated in the desired orientation. The resulting construct containing the HCR upstream of the ApoE promoter and exon/intron sequence was designated pHCR-HEP.

The approximately 2.2 kb HCR enhancer-promoter-intron cassette was excised from pHCR-HEP as either a PstI-EcoRI fragment or a HindIII-EcoRI fragment. Each of these fragments were ligated into pBIISK+ (Stratagene Corp., La Jolla, Calif.) to generate the plasmids PHCR-HEP BS (PE) (PstI-EcoRI fragment) and pHCR-HEP BS (HE) (HindIII-EcoRI fragment).

The eukaryotic expression vector V19-10 was used as a template for amplification of the SV40 polyA+ signal. This vector was constructed by inserting a 592 base pair AatII/ClaI fragment containing the origin of replication sequence from bacteriophage M13 into the eukaryotic expression vector V19-8 (described in WO 91/05795, published May 2, 1991). The 242 base pair polyA+ sequence from V19-10 was amplified as a NotI-SacII fragment or a HindIII-XhoI fragment using PCR. The primers used for PCR amplification were:

NotI-SacII fragment:

Primer 1: CTCTAGAAAGCTTAATTCAGTC (SEQ ID NO: 2)

Primer 2: TCCCCGCGGGGAAGAGCGCA-GAGCTCGG (SEQ ID NO: 3).

Thirty cycles of amplification were conducted as follows: Denaturation was at 94° C. for 30 seconds; annealing was at 56° C. for 30 seconds; and extension was at 72° C. for 30 seconds.

HindIII-XboI fragment:

Primer 3: CTCTAGAAAGCTTAATTCAGTC (SEQ ID NO: 4)

Primer 4: CTGGATCTCGAGGTACCCGGGGATCAT-AATC (SEQ ID NO: 5)

Thirty cycles of amplification were conducted as follows: Denaturation was at 94° C. for 30 seconds; annealing was at 57° C. for 30 seconds; and extension was at 72° C. for 30 seconds.

The PCR fragments were sequenced and showed 100% homology to the template. The fragments were then subcloned into NotI-SacII cut or HindIII-XhoI cut pBIISK+, to generate the plasmids pBS-PA (NS) and pBS-PA (HX), respectively.

The human IL-8 cDNA was obtained by screening a human peripheral blood lymphocyte cDNA library, prepared as follows:

Peripheral blood lymphocytes were isolated from freshly prepared buffy coats, on a ficol-paque step gradient (Pharmacia, Uppsala, Sweden). Mononuclear cells present in the interphase of the gradient were removed and washed with PBS three times. The cells were then suspended in the medium RPMI 1640+10% FCS (fetal calf serum). About 5 million cells/ml were incubated with pokeweed mitogen (10 ug/ml, Sigma Chemical Corp., St. Louis, Mo.) for 19 hours, followed by addition of cycloheximide to a final concentration of 10 ug/ml for an additional 6 hours. Incubation was carried out at 37° C. and 5% $CO_2$.

Total RNA was isolated from activated lymphocytes using the guanidium thiocyanate-CsCl technique (Chirgwin et al., *Biochem.*, 18: 5294–5299 [1979]). Polyadenylated RNA was selected by oligo(dT) chromatography. The polyA+ RNA was then ethanol precipitated and centrifuged. The final pellet was dissolved in water and kept in liquid nitrogen in aliquots.

About 5 ug of polyA+ RNA were used for cDNA library construction. After denaturation with methyl mercury hydroxide, oligo(dT)-primed double strand cDNA was synthesized following the procedure set forth in Sambrook et al., supra, followed by methylation with EcoRI and Alu methylases. The technique of Dorssers et al, (*Nuc. Acid. Res.*, 15: 3629, [19AFM]) was used to introduce EcoRI and HindIII sites on the 5' and 3' ends of the cDNAs, respectively. After digestion with EcoRI and HindIII restriction enzymes, cDNAs that were larger than 500 base pairs were isolated from an agarose gel by electroelution. The eukaryotic expression vector V19-10 (described above), was digested with EcoRI and HindIII and was then ligated with the cDNAs. These new plasmids containing cDNA inserts were transfected into competent DH5 alpha cells (GIBCO-BRL, Gaithersburg, Md.). The cDNA library was frozen in aliquots at −80° C. after addition of DMSO to 7% (Okayama & Berg, *Mol. Cell. Biol.*, 2: 161–170, 1982).

A mixed oligonucleotide probe was designed on the basis of similarity in nucleotide sequences surrounding and coding for the signal peptidase cleavage site of a number of cytokines. The sequence of this degenerate probe was:

ATGTCGACMWCSVTGCMCCHRYMYSMYCYA (SEQ ID NO: 6).

In this sequence, M, W, S, V, R, Y, and H represent degenerate nucleotides. M represents A or C; W represents A or T; S represents C or G; V represents A or C or G; R represents A or G; Y represents C or T; and H represents A or C or T.

Using this probe, a cDNA encoding IL-8 was obtained and sequenced for homology comparison to the published sequence for IL-8 (Furutani et al., Biophys. Biochem. Res. Comm., 159:249–255 [1989]). The IL-8 cDNA clone was then used as a template to PCR amplify a SpeI-NotI fragment of the cDNA. Amplification was accomplished using the following oligonucleotide primers:

Primer 5: GGACTAGTCCAGAGCACACAAGCTTCTAG (SEQ ID NO: 7)

Primer 6: ATAAGAATGCGGCCGCTAAACTATTGCATCTGGCAACCC (SEQ ID NO: 8).

Thirty cycles of amplification were conducted as follows: Denaturation was at 94° C. for 30 seconds; annealing was at 54° C. for 30 seconds; and extension was at 72° C. for 30 seconds.

The amplified fragment was then subcloned into SpeI-NotI cut pIIBS-PA (NS) to produce the plasmid pIL-8 PA. The amplified IL-8 sequence, which lacked a portion of the 3' untranslated sequence of the original IL-8 cDNA, was sequence verified and found to be 100% homologous to human IL-8 in the coding region.

The polyadenylated IL-8 cDNA was put under the control of the HCR enhancer and the ApoE promoter by excising the HCR-ApoE promoter-intron cassette from the vector pHCR-HEP BS(HE) as a XhoI-SpeI fragment. This fragment was then subcloned into XhoI-SpeI cut pIL-8 PA to generate the plasmid pHCR-HEP IL-8 PA (abbreviated HE8).

For microinjection, the plasmid HE8 was digested with restriction enzymes XhoI, ScaI and AflIII, and the approximately 3.3 Kb XhoI-AflIII insert fragment containing the HCR, the ApoE promoter, the ApoE first exon, first intron, a portion of the second exon, the human IL-8 cDNA and the SV40 poly-adenylation signal was purified on a 0.8% ultra-pure DNA agarose gel (BRL Corp., Bethesda, Md.) and diluted to 1 ng/ul in 5 mM Tris, pH 7.4, 0.2 mM EDTA. About 2 to 3 picoliters of this solution were injected into the male pronucleus of each mouse embryo.

To prepare a liver expression vector to make transgenic mammals containing the transgenes KGF or MCP-1, the approximately 242 base pair HindIII-XhoI insert fragment from pBS PA (HX) was isolated and subcloned into HindIII-XhoI cut pHCR-HEP BS (PE). The resulting vector, pliv (BSK), has a polylinker region containing EcoRI, EcoRV, and HindIII restriction sites downstream of the HCR-ApoE promoter-intron cassette and upstream of the SV40 poly-adenylation signal.

B. Preparation of Embryos and Microinjection

Pregnant mare's serum ("PMS"), supplying Follicle Stimulating Hormone ("FSH") was administered to female mice of the strain BDF1 (Charles River Labs, Boston, Mass.) about three days prior to the day of microinjection. PMS (obtained from Sigma Chemicals) was prepared as a 50 I.U./ml solution in Phosphate Buffered Saline and injected intraperitoneally at 0.1 ml (5 I.U.) per animal. Human Chorionic Gonadotropin ("HCG"), supplying Luteinizing Hormone ("LH") was administered 45–48 hours after the PMS injections. HCG was also prepared as a 50 I.U./ml solution in PBS and injected IP (intraperitoneally) at 0.1 ml per animal. Females were placed with stud males of the same strain immediately after HCG injections. After mating, the females were examined for a vaginal copulation plug. The appearance of an opaque white plug indicated a successful mating.

Successfully mated females were sacrificed by cervical dislocation, and both oviducts were rapidly removed and placed in M2 medium (Hogan et al., eds., *Manipulating the Mouse Embryo: A Laboratory Manual*, Cold Spring Harbor Laboratory Press, pp 249–257 [1986]). The oviducts were transferred individually from M2 medium to PBS containing 300 µg/ml hyaluronidase (Sigma Corp., St. Louis, Mo.) in a round bottom dissection slide. The embryos were teased out of the oviduct and allowed to settle at the bottom of the slide as the cumulus cells detached from the embryos. When the cumulus masses were disaggregated (about 5 minutes) the embryos were transferred through two washes of M2 medium and the fertilized embryos were separated from unfertilized and abnormal embryos. The fertilized embryos were then transferred through 5% $CO_2$ equilibrated M16 medium (Hogan et al., supra), placed in equilibrated microdrop dishes containing M16 medium under paraffin oil and returned to the incubator.

Fertilized single-cell embryos from BDF1 xBDF1-bred mice were selected in M16 medium and incubated about 5 hours at 37° C. until the pronuclei appeared. Embryos were then transferred into M2 medium in a shallow depression slide under paraffin oil and placed under the microscope. The pronuclei were easily visible under 200x magnification. Using suction on the holding pipet, a single embryo was selected and rotated such that the male pronucleus was away from the holding pipet. Approximately 2 to 3 picoliters of solution containing the DNA construct at about 1 microgram per ml was injected into one of the pronuclei, preferably the male pronucleus. Following the injection, the embryos were returned to incubation for 18 hours and reimplanted the next day into foster pseudopregnant females.

Reimplantations were performed on anesthetized female mice of strain CD1 using a dissecting microscope. A pseudopregnant female mouse was anaesthetized with 0.017–0.020 ml/g body weight of avertin, injected IP. The mouse was placed under the dissecting microscope and the incision area was disinfected with 70% ethanol. The ovary was exteriorized and the bursal sac that surrounds the ovary and the oviduct was carefully pulled open. The ovary and oviduct were separated to expose the opening of the oviduct (termed the infindibulum). Surviving embryos were then removed from the incubator and loaded into the reimplantation pipet. The tip of the pipet was inserted several millimeters into the infindibulum and gentle pressure was used to deliver the embryos into the oviduct. About 10 to 20 2-cell embryos were implanted per mouse, resulting in a litter size of about 3 to 12. The ovary then was returned to the peritoneum, and the body wall and then the skin were sutured.

C. Identification of Transgenic Mice

Of 52 mice born after embryo injections, 9 contained the IL-8 transgene as assayed by PCR amplification. About 1 cm of the tail of each mouse was removed, and DNA was prepared using the technique set forth by Hogan et al., supra. The DNA was then subjected to PCR analysis using the following primers:

Primer 7: GCCTCTAGAAAGAGCTGGGAC (SEQ ID NO: 9)

Primer 8: CGCCGTGTTCCATTTATGAGC (SEQ ID NO: 10).

The PCR amplification procedure was denaturation at 94° C. for 30 seconds, annealing at 56° C. for 30 seconds, and extension at 72° C. for 30 seconds. Thirty cycles were performed.

The resultant transgenic mice harboring the transgene in their genome are termed the founder mice. The founder mice were backcrossed to strain BDF1 mice to generate heterozygous F1 transgenic mice.

To evaluate the F1 transgenic mice for the presence and effect of IL-8, blood was obtained and analyzed as follows.

Figure 3A:
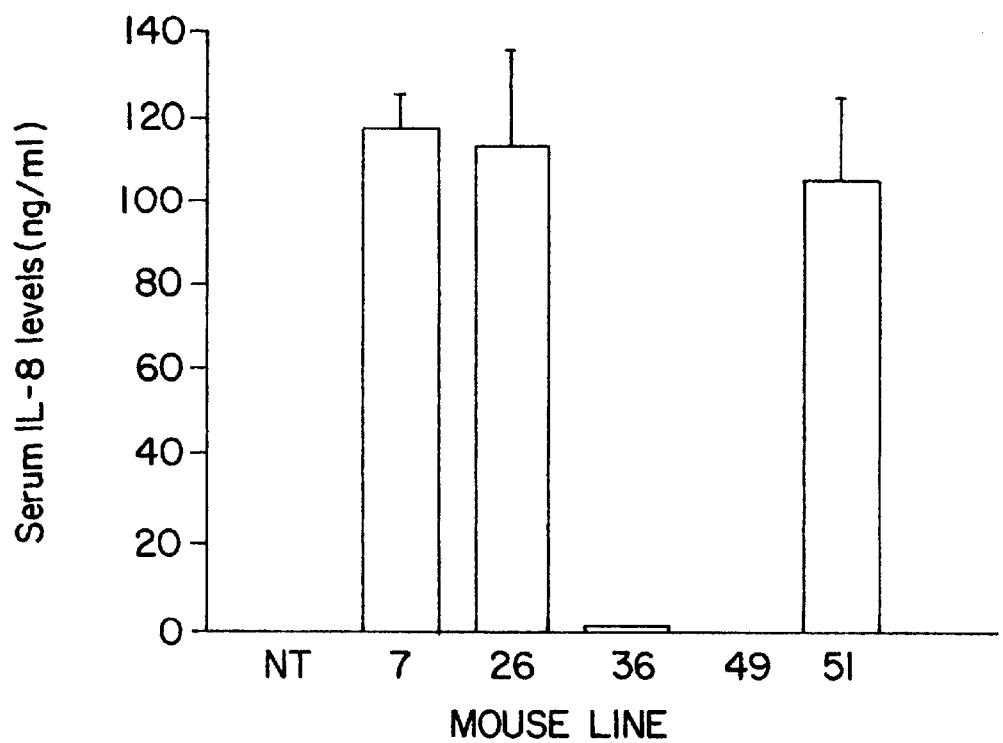
FIG. 3A shows serum IL-8 levels.

Quantitation of serum IL-8 levels were determined using an Elisa kit for human IL-8 (obtained from Biosource International, Camarillo, Calif.) and following the manufacturer's protocol. The results are shown in FIG. 3A. As can be seen, three of the lines of F1 transgenic mice (HE8 lines 7, 26, and 51) had levels of about 100 ng/ml or higher, while no IL-8 was detected in the serum of the non-transgenic (NT) mice.

Figure 3B:
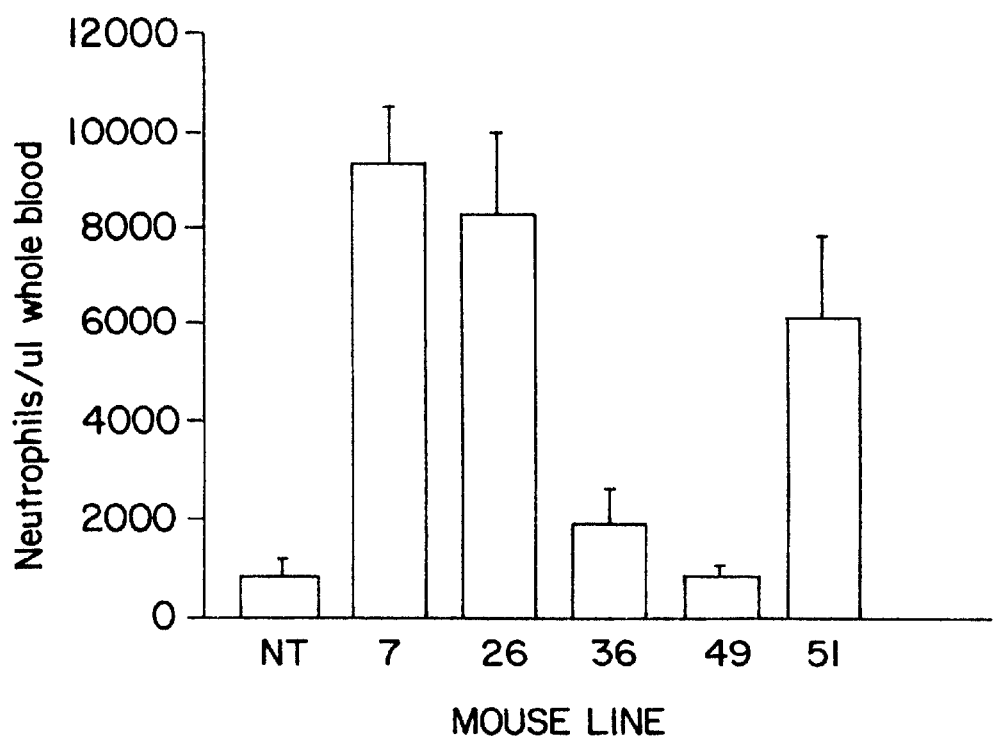
FIG. 3B shows circulating neutrophil levels. NT represents non-transgenic (control) mice. The numbers refer to individual lines of transgenic mice used in the analysis.

Circulating white blood cells in the serum of the F1 transgenic and non-transgenic mice were counted using a Sysmex F-800 blood cell counter (Toa Medical Electronics Co., LTD, Kobe, Japan) and following the manufacturer's protocol. Prior to counting, red blood cells were lysed with Quicklyser™ (Toa Medical Electronics Co., LTD, Kobe, Japan), following the manufacturer's protocol. For differential leukocyte analysis, about 3 µl of whole blood were spread on a glass slide and subjected to Wright's-Giemsa staining. At least 100 cells were counted from each slide by visualizing the cells under a 100× oil emersion lens on an Olympus CH2 student microscope. Neutrophils were distinguished from lymphocytes, macrophages, eosinophils, and basophils by their multinucleated structures. For all lines reported, at least five individual F1 heterozygotes were bled and analyzed. Absolute neutrophil levels were determined by multiplying the percentage of neutrophils on the Wright's-Giemsa stained slides by the total white blood cell count obtained from the Sysmex counter. The results are shown in FIG. 3B. Three of the F1 transgenic lines evaluated (HE8 lines 7, 26, and 51) had a circulating neutrophil level of greater than 6,000/µl blood, while the non-transgenic (NT) mice had a level of under 1,000/µl blood.

Example 2

Preparation of a HCR-KGF Transaenic Mouse

The gene encoding human KGF (keratinocyte growth factor) was obtained by PCR amplification of the gene from a normal human dermal fibroblast cDNA library. PCR amplification of KGF was accomplished using the following two oligonucleotide primers:

Primer 9: CAATCTACAATTCACAGA (SEQ ID NO: 11)

Primer 10: TTAAGTTATTGCCATAGG (SEQ ID NO: 12). The conditions for PCR were: denaturation at 92° C. for 20 seconds; anneal at 55–40° C. for 20 seconds (this consisted of 2 cycles at 55° C., followed by 2 cycles at 45° C., which was followed by 28 cycles at 40° C.); and extension at 72° C. for 30 seconds. Thirty cycles total were performed.

To introduce HindIII and BglII restriction sites to the ends of the KGF cDNA, the cDNA was PCR amplified using the following two oligonucleotide primers:

Primer 11: AACAAAGCTTCTACAATTCACAGATAGGA (SEQ ID NO: 13)

Primer 12: AACAAGATCTTAAGTTATTGCCATAGG (SEQ ID NO: 14). The conditions for PCR were: denaturation at 92° C. for 20 seconds; anneal at 45° C. for 20 seconds; and elongation at 72° C. for 30 seconds. Thirty cycles were performed.

After amplification, the KGF cDNA was purified and digested with HindIII and BglII, and then ligated into the vector pCFM3006. This vector was prepared from the ector pCFM836 (described in U.S. Pat. No. 4,710,473, issued Dec. 1, 1987). The two endogenous NdeI restriction sites in pCFM836 were removed by cutting pCFM836 with NdeI, filling in the cut ends of the vector using T4 polymerase, and then re-ligating the vector by blunt end ligation. Next, the DNA sequence between the AatII and KpnI sites of the now modified pCFM836 was altered using the technique of PCR overlapping oligonucleotide mutagenesis. The following changes at the base pair positions listed were made (the base pair position changes are relative to the BglII site on pFM836 which is position #180):

| plasmid bp # | bp changed |
|---|---|
| #428 | G/C |
| #509 | A/T |
| #617 | insert two G/C bp |
| #978 | C/G |
| #992 | A/T |
| #1002 | C/G |
| #1005 | T/A |
| #1026 | T/A |
| #1045 | T/A |
| #1176 | T/A |
| #1464 | T/A |
| #2026 | bp deletion |
| #2186 | T/A |
| #2479 | T/A |
| #2498–2501 | GTCA |
| #2641–2647 | bp deletion |

-continued

| plasmid bp # | bp changed |
|---|---|
| #3441 | A/T |
| #3649 | T/A |

The KGF cDNA in this vector was used as a template for amplification. A 710 base pair HindIII fragment of KGF was amplified using PCR and the following two oligonucleotide primers:

Primer 13: CGATCGTAAGCTTGGTCAATGACCTAG-GAGTAAC (SEQ ID NO: 15)

Primer 14: CGATCGTAAGCTTGCGGATCCTAAGT-TATTGCC (SEQ ID NO: 16).

Amplification was conducted for 30 cycles. Denaturation was at 94° C. for 30 seconds, annealing was at 58° C. for 20 seconds, and elongation was at 72° C. for 30 seconds. The amplified fragment was purified by agarose gel electrophoresis and then ligated into the vector plivBsk (described in Example 1; shown in FIG. 2). E. coli cells were then transformed with the ligation mixture and plated out for overnight incubation. After incubation, colonies were selected, grown up, and the plasmids analyzed for those containing KGF in the proper orientation. The orientation of the plasmid KGF was determined by restriction endonuclease digestion with EcoRI. Clones with the proper orientation were grown up and the plasmid purified using a Qiagen column (Qiagen Corp., Chatsworth, Calif.). Several clones were sequenced to verify the orientation and sequence of the KGF.

DNA to be used in microinjection of the embryos was prepared by cutting the vector containing KGF with SpeI and XhoI to obtain a DNA fragment containing (in order) the HCR, ApoE promoter, KGF, and polyA sequences. This DNA was gel purified and prepared as described in Example 1. Microinjection and implantation into pseudopregnant mice were as described in Example 1.

Example 3

Preparation of a HCR-MCP-1 Transaenic Mouse

The cDNA encoding human MCP-1 was obtained by screening the human peripheral blood lymphocyte library described in Example 1 with the following probe:

CTGTSYCTSCTSNTSMTWGTWGCYGSCT (SEQ ID NO: 17).

In the probe sequence, S represents C or G; Y represents T or C; N represents A or T or C or G; M represents C or A; and W represents A or T.

A clone of about 850 base pairs was obtained using this probe and was inserted into the vector V19-8 (described in Example 1). This clone was then sequenced for identification, and found to be homologous to the published sequence for MCP-1 (Matsushima et al., J. Exp. Med., 167:1883–1893 [1988]).

The MCP-1 cDNA was excised from the vector V19-8 as an approximately 350 base pair EcoRI-PstI fragment, and was ligated into the vector pUC19 previously cut with EcoRI and HindIII. The cDNA was then removed as an EcoRI-HindIII fragment and inserted into the vector plivBSK. The vector containing the cDNA was called HEMF. This vector was transformed into E. coli strain DH5 alpha for amplification. After culturing the cells overnight, the plasmid was isolated and purified using the alkaline lysis method, followed by cesium chloride centrifugation.

After centrifugation, the plasmid was digested with the restriction enzymes SpeI, XhoI, and ScaI, and the approximately 2.8 kilobase DNA fragment containing the HCR, ApoE promoter and first intron, MCP-1 cDNA, and the SV40 polyA sequence was isolated. This DNA was gel purified and prepared for microinjection as described in Example 1. Microinjection of embryos and implantation of embryos into pseudopregnant mice were as described in Example 1.

Of 130 offspring analyzed, 5 contained the MCP-1 transgene as detected using PCR analysis.

Example 4

Preparation of a HCR-AFM Transgenic Mouse

The cDNA encoding human AFM was obtained as follows:

The polymerase chain reaction (PCR) was used to amplify a portion of the cDNA encoding AFM. PCR was first performed in a total volume of about 100 μl using approximately one nanogram of Quick Clone human liver cDNA (Clontech, cat. no. 7113-1) as the template and standard PCR buffer (Perkin-Elmer Cetus). About 1 uM of each of the following two degenerate primers was also used in this PCR reaction.

ACGCTGAATTCGCCARAARTTYATHGARGAYAA (SEQ ID NO:18)

ACGCTAAGCTTGCRTCYTTRTADATYTGNACDAT (SEQ ID NO:19).

In these primer sequences, R represents A or G; Y represents T or C; N represents A or T or C or G; D represents G or A or T; H represents A or C or T.

The conditions used for the PCR reaction were as follows: 95° C. for 8 min (1 cycle); 94° C. for 1 min, 34° C. for 10 min and 72° C. for 2 min (3 cycles); 94° C. for 1 min, 50° C. for 1 min, and 72° C. for 2 min (45 cycles); 72° C. for 5 min (1 cycle).

An approximately 1 μl aliquot of amplified DNA obtained from this PCR was used as a template for a second PCR using a nested primer pair. For this second PCR, the following degenerate primers were used:

ACGCTGAATTCGCGAYAAYATHGARTAYATHAC (SEQ ID NO:20)

ACGCTAAGCTTGCNGARTAYTCRAANGTRAA (SEQ ID NO:21).

In these primer sequences, R represents A or G; Y represents T or C; H represents A or C or T; N represents A or T or C or G.

This second PCR was performed using the same reaction mix and cycling parameters as for the first PCR. Analysis of this second PCR by agarose gel electrophoresis revealed the amplification of an approximately 1 kb DNA fragment. This DNA fragment was gel purified, and then digested with restriction endonucleases EcoRI and HindIII, and ligated into the cloning/sequencing vector mp19 (Boehringer Mannheim Corporation) for sequencing.

An oligonucleotide identical to a small portion of the sequence of the DNA fragment was generated and used to isolate the full-length AFM cDNA from a human liver cDNA library (Clonetech, cat no. HL1115a). The sequence of this oligonucleotide was:

TATGTGCTATGGAGGGGC (SEQ ID NO:22).

Positive clones from this library screening were purified using standard procedures and then re-screened with the same oligonucleotide probe, and a single clone (called 17AFM) containing an approximately 2.3 kb insert was selected. This clone was inserted into the vector pGem3Z for sequencing to confirm that it encoded the full-length cDNA for human AFM. The nucleic acid sequence and translated amino acid sequence for this clone are set forth in FIG. 4.

To prepare a transgenic mouse containing the transgene human AFM, the AFM cDNA clone was removed from the vector by digesting with EcoRI. The cDNA was then inserted into the vector plivBSK (described in Example I). This vector containing the AFM cDNA, was transformed into *E. coli* strain DH5 alpha for amplification. After culturing the cells overnight, the plasmid was isolated and purified using the standard alkaline lysis method, followed by cesium chloride centrifugation.

After centrifugation, the plasmid was digested with the restriction enzymes SpeI, XhoI, and ScaI, and the DNA fragment containing the HCR, ApoE promoter and first intron, AFM cDNA and the SV40 polyA sequence was isolated. This DNA was gel purified and prepared for microinjection as described in Example I.

Microinjection and implantation of embryos into pseudopregnant mice were as described in Example I.

All literature cited herein is expressly incorporated by reference.

We claim:

1. A nucleic acid sequence comprising the hepatocyte-specific control region (HCR) enhancer sequence disclosed in SEQ ID NO 1 or a biologically active fragment thereof, operably linked to a promoter and a transgene, wherein the transgene comprises a nucleotide sequence encoding a polypeptide involved in immune response, hematopoiesis, inflammation, cell growth and proliferation, cell lineage differentiation, or stress response, and wherein the promoter is selected from the group of promoters consisting of the promoters of: ApoA-I, ApoA-II, ApoA-III, ApoA-IV, ApoB-100, ApoC-I, ApoC-II, ApoC-III, ApoE, albumin, alpha feto protein, PEPCK, transthyretin, SV40, CMV and TK.

2. The nucleic acid sequence of claim 1 wherein the polypeptide is selected from the group consisting of: interleukin 1, interleukin 2, interleukin 3, interleukin 4, interleukin 5, interleukin 6, interleukin 7, interleukin 8, interleukin 9, interleukin 10, interleukin 11, interleukin 12, ENA-78, interferon-α, interferon-β, interferon-γ, granulocyte-colony stimulating factor, granulocyte-macrophage colony stimulatory factor, macrophage colony stimulating factor, stem cell factor, keratinocyte growth factor (KGF), afamin (AFM), monocyte chemoattractant protein (MCP-1), tumor necrosis factor (TNF), and biologically active fragments thereof.

3. A nucleic acid sequence comprising the HCR enhancer sequence disclosed in SEQ ID NO 1 or a biologically active fragment thereof, the human ApoE promoter, the human ApoE intron 1 operatively linked at its 5' end to the human ApoE exon 1 and at its 3' end to a segment of the human ApoE exon 2 wherein the ApoE exon 2 segment comprises the 5' sequences of the ApoE exon 2, and a nucleotide sequence encoding human IL-8.

4. A nucleic acid sequence comprising the HCR enhancer sequence disclosed in SEQ ID NO 1 or a biologically active fragment thereof, the human ApoE promoter, the human ApoE intron 1 operatively linked at its 5' end to the human ApoE exon 1 and at its 3' end to a segment of the human ApoE exon 2 wherein the ApoE exon 2 segment comprises the 5' sequences of the ApoE exon 2, and the nucleotide sequence encoding human KGF.

5. A nucleic acid sequence comprising the HCR enhancer sequence disclosed in SEQ ID NO 1 or a biologically active fragment thereof, the human ApoE promoter, the human ApoE intron 1 operatively linked at its 5' end to the human ApoE exon 1 and at its 3' end to a segment of the human ApoE exon 2 wherein the ApoE exon 2 segment comprises the 5' sequences of the ApoE exon 2, and the nucleotide sequence encoding human MCP-1.

6. A vector comprising the nucleic acid sequence of claim 1.

7. A vector comprising the nucleic acid sequence of claim 2.

8. A vector comprising the nucleic acid sequence of claim 3.

9. A vector comprising the nucleic acid sequence of claim 4.

10. A vector comprising the nucleic acid sequence of claim 5.

11. A recombinant prokaryotic host cell comprising the nucleic acid of claims 1, 2, 3, 4, or 5.

12. A recombinant eukaryotic host cell comprising the nucleic acid of claims 1, 2, 3, 4, or 5.

13. A recombinant prokaryotic host cell comprising the vector of claims 6, 7, 8, 9, or 10.

14. A recombinant eukaryotic host cell comprising the vector of claims 6, 7, 8, 9, or 10.

* * * * *

UNITED STATES PATENT AND TRADEMARK OFFICE
CERTIFICATE OF CORRECTION

PATENT NO. : 6,268,212 B1
DATED : July 31, 2001
INVENTOR(S) : William Scott Simonet It is certified that error appears in the above-identified patent and that said Letters Patent is hereby corrected as shown below:

Column 14,
Line 47, change "Xbol" to -- Xhol --

Column 18,
Line 10, change "Transaenic" to -- Transgenic --.
Line 38, change "ector" to -- vector --.
Line 49, change "pFM836" to -- pCFM836 --.

Column 19,
Line 43, change "Transaenic" to -- Transgenic --.

Signed and Sealed this

Twenty-first Day of May, 2002

Attest:

JAMES E. ROGAN
Director of the United States Patent and Trademark Office

Attesting Officer

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
       (A) LENGTH: 774 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:1:

```
CTGCAGGCTC AGAGGCACAC AGGAGTTTCT GGGCTCACCC TGCCCCCTTC CAACCCCTCA      60

GTTCCCATCC TCCAGCAGCT GTTTGTGTGC TGCCTCTGAA GTCCACACTG AACAAACTTC     120

AGCCTACTCA TGTCCCTAAA ATGGGCAAAC ATTGCAAGCA GCAAACAGCA AACACACAGC     180

CCTCCCTGCC TGCTGACCTT GGAGCTGGGG CAGAGGTCAG AGACCTCTCT GGGCCCATGC     240

CACCTCCAAC ATCCACTCGA CCCCTTGGAA TTTCGGTGGA GAGGAGCAGA GGTTGTCCTG     300

GCGTGGTTTA GGTAGTGTGA GAGGGTCCGG GTTCAAAACC ACTTGCTGGG TGGGGAGTCG     360

TCAGTAAGTG GCTATGCCCC GACCCCGAAG CCTGTTTCCC CATCTGTACA ATGGAAATGA     420

TAAAGACGCC CATCTGATAG GGTTTTTGTG GCAAATAAAC ATTTGGTTTT TTTGTTTTGT     480

TTTGTTTTGT TTTTTGAGAT GGAGGTTTGC TCTGTCGCCC AGGCTGGAGT GCAGTGACAC     540

AATCTCATCT CACCACAACC TTCCCCTGCC TCAGCCTCCC AAGTAGCTGG GATTACAAGC     600

ATGTGCCACC ACACCTGGCT AATTTTCTAT TTTTAGTAGA GACGGGTTTC TCCATGTTGG     660

TCAGCCTCAG CCTCCCAAGT AACTGGGATT ACAGGCCTGT GCCACCACAC CCGGCTAATT     720

TTTTCTATTT TTGACAGGGA CGGGGTTTCA CCATGTTGGT CAGGCTGGTC TAGA           774
```

(2) INFORMATION FOR SEQ ID NO:2:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:2:

```
CTCTAGAAAG CTTAATTCAG TC                                               22
```

(2) INFORMATION FOR SEQ ID NO:3:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:3:

TCCCCGCGGG GAAGAGCGCA GAGCTCGG                                                  28

(2) INFORMATION FOR SEQ ID NO:4:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:4:

CTCTAGAAAG CTTAATTCAG TC                                                        22

(2) INFORMATION FOR SEQ ID NO:5:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:5:

CTGGATCTCG AGGTACCCGG GGATCATAAT C                                              31

(2) INFORMATION FOR SEQ ID NO:6:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:6:

ATGTCGACMW CSVTGCMCCH RYMYSMYCYA                                                30

(2) INFORMATION FOR SEQ ID NO:7:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:7:

GGACTAGTCC AGAGCACACA AGCTTCTAG                                                 29

(2) INFORMATION FOR SEQ ID NO:8:

(i) SEQUENCE CHARACTERISTICS:
            (A) LENGTH: 39 base pairs
            (B) TYPE: nucleic acid
            (C) STRANDEDNESS: single (D) TOPOLOGY: linear (ii) MOLECULE TYPE: cDNA (xi) SEQUENCE DESCRIPTION: SEQ ID NO:8:

ATAAGAATGC GGCCGCTAAA CTATTGCATC TGGCAACCC          39

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

GCCTCTAGAA AGAGCTGGGA C          21

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

CGCCGTGTTC CATTTATGAG C          21

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

CAATCTACAA TTCACAGA          18

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

TTAAGTTATT GCCATAGG          18

(2) INFORMATION FOR SEQ ID NO:13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

AACAAAGCTT CTACAATTCA CAGATAGGA                                                29

(2) INFORMATION FOR SEQ ID NO:14:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:14:

AACAAGATCT TAAGTTATTG CCATAGG                                                  27

(2) INFORMATION FOR SEQ ID NO:15:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:15:

CGATCGTAAG CTTGGTCAAT GACCTAGGAG TAAC                                          34

(2) INFORMATION FOR SEQ ID NO:16:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:16:

CGATCGTAAG CTTGCGGATC CTAAGTTATT GCC                                           33

(2) INFORMATION FOR SEQ ID NO:17:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:17:

CTGTSYCTSC TSNTSMTWGT WGCYGSCT                                                 28

(2) INFORMATION FOR SEQ ID NO:18:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:18:

ACGCTGAATT CGCCARAART TYATHGARGA YAA                                           33

(2) INFORMATION FOR SEQ ID NO:19:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

ACGCTAAGCT TGCRTCYTTR TADATYTGNA CDAT                              34

(2) INFORMATION FOR SEQ ID NO:20:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

ACGCTGAATT CGCGAYAAYA THGARTAYAT HAC                               33

(2) INFORMATION FOR SEQ ID NO:21:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

ACGCTAAGCT TGCNGARTAY TCRAANGTRA A                                 31

(2) INFORMATION FOR SEQ ID NO:22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

TATGTGCTAT GGAGGGGC                                                    18

(2) INFORMATION FOR SEQ ID NO:23:

(i) SEQUENCE CHARACTERISTICS:
        (A) LENGTH: 2287 base pairs
        (B) TYPE: nucleic acid
        (C) STRANDEDNESS: unknown
        (D) TOPOLOGY: unknown (ii) MOLECULE TYPE: cDNA (ix) FEATURE:
        (A) NAME/KEY: CDS
        (B) LOCATION: 318..2117

(ix) FEATURE:
        (A) NAME/KEY: mat_peptide
        (B) LOCATION: 381..2114

-continued (ix) FEATURE:
    (A) NAME/KEY: sig_peptide
    (B) LOCATION: 318..380

(xi) SEQUENCE DESCRIPTION: SEQ ID NO:23:

```
CCCCGAGTCT CTGCGCCTTC ACATAGTTGT CACAGGACTA AAGCAAATTG ATCCAGGGGG      60

AAACACTGTA GACCGTGTAT ATAAAAACAC TCTATAAACT GCAATGCTCA ATTCTTAGTA     120

TAACTATTGT TGTTGTATTG ATATTTATTA GTATTGGTGC TCACAAAAAG AGTCTAAATT     180

CCATAAGTCT TTATATTCAG GCTACTCTTT ATTTTTGAAA ACTCATTTTC TATCACCTTT     240

TTCTATTTTA CTCCATATTG AGGCCTCATA AATCCAATTT TTATTTCTT TCTTTTGTAA      300

ATGTGGTTTC TACAAAG ATG AAA CTA CTA AAA CTT ACA GGT TTT ATT TTT        350
                   Met Lys Leu Leu Lys Leu Thr Gly Phe Ile Phe
                   -21 -20                  -15

TTC TTG TTT TTT TTG ACT GAA TCC CTA ACC CTG CCC ACA CAA CCT CGG       398
Phe Leu Phe Phe Leu Thr Glu Ser Leu Thr Leu Pro Thr Gln Pro Arg
-10              -5                   1                  5

GAT ATA GAG AAC TTC AAT AGT ACT CAA AAA TTT ATA GAA GAT AAT ATT       446
Asp Ile Glu Asn Phe Asn Ser Thr Gln Lys Phe Ile Glu Asp Asn Ile
               10                  15                  20

GAA TAC ATC ACC ATC ATT GCA TTT GCT CAG TAT GTT CAG GAA GCA ACC       494
Glu Tyr Ile Thr Ile Ile Ala Phe Ala Gln Tyr Val Gln Glu Ala Thr
        25                  30                  35

TTT GAA GAA ATG GAA AAG CTG GTG AAA GAC ATG GTA GAA TAC AAA GAC       542
Phe Glu Glu Met Glu Lys Leu Val Lys Asp Met Val Glu Tyr Lys Asp
    40                  45                  50

AGA TGT ATG GCT GAC AAG ACG CTC CCA GAG TGT TCA AAA TTA CCT AAT       590
Arg Cys Met Ala Asp Lys Thr Leu Pro Glu Cys Ser Lys Leu Pro Asn
55                  60                  65                  70

AAT GTT TTA CAG GAA AAA ATA TGT GCT ATG GAG GGG CTG CCA CAA AAG       638
Asn Val Leu Gln Glu Lys Ile Cys Ala Met Glu Gly Leu Pro Gln Lys
                75                  80                  85

CAT AAT TTC TCA CAC TGC TGC AGT AAG GTT GAT GCT CAA AGA AGA CTC       686
His Asn Phe Ser His Cys Cys Ser Lys Val Asp Ala Gln Arg Arg Leu
            90                  95                  100

TGT TTC TTC TAT AAC AAG AAA TCT GAT GTG GGA TTT CTG CCT CCT TTC       734
Cys Phe Phe Tyr Asn Lys Lys Ser Asp Val Gly Phe Leu Pro Pro Phe
        105                 110                 115

CCT ACC CTG GAT CCC GAA GAG AAA TGC CAG GCT TAT GAA AGT AAC AGA       782
Pro Thr Leu Asp Pro Glu Glu Lys Cys Gln Ala Tyr Glu Ser Asn Arg
    120                 125                 130

GAA TCC CTT TTA AAT CAC TTT TTA TAT GAA GTT GCC AGA AGG AAC CCA       830
Glu Ser Leu Leu Asn His Phe Leu Tyr Glu Val Ala Arg Arg Asn Pro
135                 140                 145                 150

TTT GTC TTC GCC CCT ACA CTT CTA ACT GTT GCT GTT CAT TTT GAG GAG       878
Phe Val Phe Ala Pro Thr Leu Leu Thr Val Ala Val His Phe Glu Glu
                155                 160                 165

GTG GCC AAA TCA TGT TGT GAA GAA CAA AAC AAA GTC AAC TGC CTT CAA       926
Val Ala Lys Ser Cys Cys Glu Glu Gln Asn Lys Val Asn Cys Leu Gln
            170                 175                 180

ACA AGG GCA ATA CCT GTC ACA CAA TAT TTA AAA GCA TTT TCT TCT TAT       974
Thr Arg Ala Ile Pro Val Thr Gln Tyr Leu Lys Ala Phe Ser Ser Tyr
        185                 190                 195

CAA AAA CAT GTC TGT GGG GCA CTT TTG AAA TTT GGA ACC AAA GTT GTA      1022
Gln Lys His Val Cys Gly Ala Leu Leu Lys Phe Gly Thr Lys Val Val
    200                 205                 210

CAC TTT ATA TAT ATT GCG ATA CTC AGT CAA AAA TTC CCC AAG ATT GAA      1070
His Phe Ile Tyr Ile Ala Ile Leu Ser Gln Lys Phe Pro Lys Ile Glu
215                 220                 225                 230
```

-continued

| | |
|---|---|
| TTT AAG GAG CTT ATT TCT CTT GTA GAA GAT GTT TCT TCC AAC TAT GAT<br>Phe Lys Glu Leu Ile Ser Leu Val Glu Asp Val Ser Ser Asn Tyr Asp<br>                          235                    240                    245 | 1118 |
| GGA TGC TGT GAA GGG GAT GTT GTG CAG TGC ATC CGT GAC ACG AGC AAG<br>Gly Cys Cys Glu Gly Asp Val Val Gln Cys Ile Arg Asp Thr Ser Lys<br>                    250                    255                    260 | 1166 |
| GTT ATG AAC CAT ATT TGT TCA AAA CAA GAT TCT ATC TCC AGC AAA ATC<br>Val Met Asn His Ile Cys Ser Lys Gln Asp Ser Ile Ser Ser Lys Ile<br>            265                    270                    275 | 1214 |
| AAA GAG TGC TGT GAA AAG AAA ATA CCA GAG CGC GGC CAG TGC ATA ATT<br>Lys Glu Cys Cys Glu Lys Lys Ile Pro Glu Arg Gly Gln Cys Ile Ile<br>280                    285                    290 | 1262 |
| AAC TCA AAC AAA GAT GAT AGA CCA AAG GAT TTA TCT CTA AGA GAA GGA<br>Asn Ser Asn Lys Asp Asp Arg Pro Lys Asp Leu Ser Leu Arg Glu Gly<br>295                    300                    305                    310 | 1310 |
| AAA TTT ACT GAC AGT GAA AAT GTG TGT CAA GAA CGA GAT GCT GAC CCA<br>Lys Phe Thr Asp Ser Glu Asn Val Cys Gln Glu Arg Asp Ala Asp Pro<br>                    315                    320                    325 | 1358 |
| GAC ACC TTC TTT GCG AAG TTT ACT TTT GAA TAC TCA AGG AGA CAT CCA<br>Asp Thr Phe Phe Ala Lys Phe Thr Phe Glu Tyr Ser Arg Arg His Pro<br>            330                    335                    340 | 1406 |
| GAC CTG TCT ATA CCA GAG CTT TTA AGA ATT GTT CAA ATA TAC AAA GAT<br>Asp Leu Ser Ile Pro Glu Leu Leu Arg Ile Val Gln Ile Tyr Lys Asp<br>                    345                    350                    355 | 1454 |
| CTC CTG AGA AAT TGC TGC AAC ACA GAA AAC CCT CCA GGT TGT TAC CGT<br>Leu Leu Arg Asn Cys Cys Asn Thr Glu Asn Pro Pro Gly Cys Tyr Arg<br>            360                    365                    370 | 1502 |
| TAC GCG GAA GAC AAA TTC AAT GAG ACA ACT GAG AAA AGC CTC AAG ATG<br>Tyr Ala Glu Asp Lys Phe Asn Glu Thr Thr Glu Lys Ser Leu Lys Met<br>375                    380                    385                    390 | 1550 |
| GTA CAA CAA GAA TGT AAA CAT TTC CAG AAT TTG GGG AAG GAT GGT TTG<br>Val Gln Gln Glu Cys Lys His Phe Gln Asn Leu Gly Lys Asp Gly Leu<br>                    395                    400                    405 | 1598 |
| AAA TAC CAT TAC CTC ATC AGG CTC ACG AAG ATA GCT CCC CAA CTC TCC<br>Lys Tyr His Tyr Leu Ile Arg Leu Thr Lys Ile Ala Pro Gln Leu Ser<br>            410                    415                    420 | 1646 |
| ACT GAA GAA CTG GTG TCT CTT GGC GAG AAA ATG GTG ACA GCT TTC ACT<br>Thr Glu Glu Leu Val Ser Leu Gly Glu Lys Met Val Thr Ala Phe Thr<br>                    425                    430                    435 | 1694 |
| ACT TGC TGT ACG CTA AGT GAA GAG TTT GCC TGT GTT GAT AAT TTG GCA<br>Thr Cys Cys Thr Leu Ser Glu Glu Phe Ala Cys Val Asp Asn Leu Ala<br>440                      445                    450 | 1742 |
| GAT TTA GTT TTT GGA GAG TTA TGT GGA GTA AAT GAA AAT CGA ACT ATC<br>Asp Leu Val Phe Gly Glu Leu Cys Gly Val Asn Glu Asn Arg Thr Ile<br>455                    460                    465                    470 | 1790 |
| AAC CCT GCT GTG GAC CAC TGC TGT AAA ACA AAC TTT GCC TTC AGA AGG<br>Asn Pro Ala Val Asp His Cys Cys Lys Thr Asn Phe Ala Phe Arg Arg<br>                    475                    480                    485 | 1838 |
| CCC TGC TTT GAG AGT TTG AAA GCT GAT AAA ACA TAT GTG CCT CCA CCT<br>Pro Cys Phe Glu Ser Leu Lys Ala Asp Lys Thr Tyr Val Pro Pro Pro<br>            490                    495                    500 | 1886 |
| TTC TCT CAA GAT TTA TTT ACC TTT CAC GCA GAC ATG TGT CAA TCT CAG<br>Phe Ser Gln Asp Leu Phe Thr Phe His Ala Asp Met Cys Gln Ser Gln<br>                    505                    510                    515 | 1934 |
| AAT GAG GAG CTT CAG AGG AAG ACA GAC AGG TTT CTT GTC AAC TTA GTG<br>Asn Glu Glu Leu Gln Arg Lys Thr Asp Arg Phe Leu Val Asn Leu Val<br>520                    525                    530 | 1982 |
| AAG CTG AAG CAT GAA CTC ACA GAT GAA GAG CTG CAG TCT TTG TTT ACA<br>Lys Leu Lys His Glu Leu Thr Asp Glu Glu Leu Gln Ser Leu Phe Thr | 2030 |

```
535                 540                 545                 550
AAT TTC GCA AAT GTA GTG GAT AAG TGC TGC AAA GCA GAG AGT CCT GAA      2078
Asn Phe Ala Asn Val Val Asp Lys Cys Cys Lys Ala Glu Ser Pro Glu
                    555                 560                 565

GTC TGC TTT AAT GAA GAG AGT CCA AAA ATT GGC AAC TGAAGCCAGC           2124
Val Cys Phe Asn Glu Glu Ser Pro Lys Ile Gly Asn
            570                 575

TGCTGGAGAT ATGTAAAGAA AAAAGCACCA AAGGGAAGGC TTCCTATCTG TGTGGTGATG    2184

AATCGCATTT CCTGAGAACA AAATAAAAGG ATTTTTCTGT AACTGTCACC TGAAATAATA    2244

CATTGCAGCA AGCAATAAAC ACAACATTTT GTAAAGTTAA AAA                      2287

(2) INFORMATION FOR SEQ ID NO:24:

(i) SEQUENCE CHARACTERISTICS:
        (A) LENGTH: 599 amino acids
        (B) TYPE: amino acid
        (D) TOPOLOGY: linear (ii) MOLECULE TYPE: protein (xi) SEQUENCE DESCRIPTION: SEQ ID NO:24:

Met Lys Leu Leu Lys Leu Thr Gly Phe Ile Phe Phe Leu Phe Phe Leu
-21 -20             -15                 -10

Thr Glu Ser Leu Thr Leu Pro Thr Gln Pro Arg Asp Ile Glu Asn Phe
-5              1               5                   10

Asn Ser Thr Gln Lys Phe Ile Glu Asp Asn Ile Glu Tyr Ile Thr Ile
            15                  20                  25

Ile Ala Phe Ala Gln Tyr Val Gln Glu Ala Thr Phe Glu Glu Met Glu
            30                  35                  40

Lys Leu Val Lys Asp Met Val Glu Tyr Lys Asp Arg Cys Met Ala Asp
            45              50              55

Lys Thr Leu Pro Glu Cys Ser Lys Leu Pro Asn Asn Val Leu Gln Glu
60              65                  70                  75

Lys Ile Cys Ala Met Glu Gly Leu Pro Gln Lys His Asn Phe Ser His
                80                  85                  90

Cys Cys Ser Lys Val Asp Ala Gln Arg Arg Leu Cys Phe Phe Tyr Asn
                95                  100                 105

Lys Lys Ser Asp Val Gly Phe Leu Pro Pro Phe Pro Thr Leu Asp Pro
        110                 115                 120

Glu Glu Lys Cys Gln Ala Tyr Glu Ser Asn Arg Glu Ser Leu Leu Asn
        125                 130                 135

His Phe Leu Tyr Glu Val Ala Arg Arg Asn Pro Phe Val Phe Ala Pro
140                 145                 150                 155

Thr Leu Leu Thr Val Ala Val His Phe Glu Glu Val Ala Lys Ser Cys
                160                 165                 170

Cys Glu Glu Gln Asn Lys Val Asn Cys Leu Gln Thr Arg Ala Ile Pro
                175                 180                 185

Val Thr Gln Tyr Leu Lys Ala Phe Ser Ser Tyr Gln Lys His Val Cys
            190                 195                 200

Gly Ala Leu Leu Lys Phe Gly Thr Lys Val Val His Phe Ile Tyr Ile
            205                 210                 215

Ala Ile Leu Ser Gln Lys Phe Pro Lys Ile Glu Phe Lys Glu Leu Ile
220                 225                 230                 235

Ser Leu Val Glu Asp Val Ser Ser Asn Tyr Asp Gly Cys Cys Glu Gly
                240                 245                 250
```

-continued

```
Asp Val Val Gln Cys Ile Arg Asp Thr Ser Lys Val Met Asn His Ile
            255                 260                 265

Cys Ser Lys Gln Asp Ser Ile Ser Ser Lys Ile Lys Glu Cys Cys Glu
            270                 275                 280

Lys Lys Ile Pro Glu Arg Gly Gln Cys Ile Ile Asn Ser Asn Lys Asp
            285                 290                 295

Asp Arg Pro Lys Asp Leu Ser Leu Arg Glu Gly Lys Phe Thr Asp Ser
300                 305                 310                 315

Glu Asn Val Cys Gln Glu Arg Asp Ala Asp Pro Asp Thr Phe Phe Ala
                320                 325                 330

Lys Phe Thr Phe Glu Tyr Ser Arg Arg His Pro Asp Leu Ser Ile Pro
            335                 340                 345

Glu Leu Leu Arg Ile Val Gln Ile Tyr Lys Asp Leu Leu Arg Asn Cys
            350                 355                 360

Cys Asn Thr Glu Asn Pro Pro Gly Cys Tyr Arg Tyr Ala Glu Asp Lys
            365                 370                 375

Phe Asn Glu Thr Thr Glu Lys Ser Leu Lys Met Val Gln Gln Glu Cys
380                 385                 390                 395

Lys His Phe Gln Asn Leu Gly Lys Asp Gly Leu Lys Tyr His Tyr Leu
                400                 405                 410

Ile Arg Leu Thr Lys Ile Ala Pro Gln Leu Ser Thr Glu Glu Leu Val
            415                 420                 425

Ser Leu Gly Glu Lys Met Val Thr Ala Phe Thr Thr Cys Cys Thr Leu
            430                 435                 440

Ser Glu Glu Phe Ala Cys Val Asp Asn Leu Ala Asp Leu Val Phe Gly
    445                 450                 455

Glu Leu Cys Gly Val Asn Glu Asn Arg Thr Ile Asn Pro Ala Val Asp
460                 465                 470                 475

His Cys Cys Lys Thr Asn Phe Ala Phe Arg Arg Pro Cys Phe Glu Ser
            480                 485                 490

Leu Lys Ala Asp Lys Thr Tyr Val Pro Pro Pro Phe Ser Gln Asp Leu
            495                 500                 505

Phe Thr Phe His Ala Asp Met Cys Gln Ser Gln Asn Glu Glu Leu Gln
            510                 515                 520

Arg Lys Thr Asp Arg Phe Leu Val Asn Leu Val Lys Leu Lys His Glu
    525                 530                 535

Leu Thr Asp Glu Glu Leu Gln Ser Leu Phe Thr Asn Phe Ala Asn Val
540                 545                 550                 555

Val Asp Lys Cys Cys Lys Ala Glu Ser Pro Glu Val Cys Phe Asn Glu
                560                 565                 570

Glu Ser Pro Lys Ile Gly Asn
            575
```